(12) United States Patent
Lavie et al.

(10) Patent No.: US 7,806,831 B2
(45) Date of Patent: Oct. 5, 2010

(54) METHOD AND APPARATUS FOR THE NON-INVASIVE DETECTION OF PARTICULAR SLEEP-STATE CONDITIONS BY MONITORING THE PERIPHERAL VASCULAR SYSTEM

(75) Inventors: Peretz Lavie, Haifa (IL); Robert P. Schnall, Kiryat Bialik (IL); Jacob Sheffy, Haifa (IL); Giora Pillar, Haifa (IL)

(73) Assignee: Itamar Medical Ltd., Caesarea (IL)

( * ) Notice: Subject to any disclaimer, the term of this patent is extended or adjusted under 35 U.S.C. 154(b) by 2545 days.

(21) Appl. No.: 10/195,464

(22) Filed: Jul. 16, 2002

(65) Prior Publication Data
US 2003/0004423 A1  Jan. 2, 2003

Related U.S. Application Data

(63) Continuation-in-part of application No. PCT/IL01/00199, filed on Mar. 1, 2001.

(60) Provisional application No. 60/305,917, filed on Jul. 16, 2001, provisional application No. 60/368,136, filed on Mar. 29, 2002, provisional application No. 60/240,079, filed on Oct. 16, 2000, provisional application No. 60/212,648, filed on Jun. 19, 2000, provisional application No. 60/186,358, filed on Mar. 2, 2000.

(51) Int. Cl.
*A61B 5/02* (2006.01)

(52) U.S. Cl. ............... 600/507; 600/483; 600/500; 600/504; 600/481

(58) Field of Classification Search ............ 600/300, 600/301, 481, 483, 500–507, 490–499, 323, 600/324, 334, 340, 363, 328
See application file for complete search history.

(56) References Cited

U.S. PATENT DOCUMENTS 3,104,661 A  9/1963  Halpern (Continued)

FOREIGN PATENT DOCUMENTS

EP  0465345  8/1992

(Continued)

OTHER PUBLICATIONS

G. Pillar, et al., "Paradoxical Effects of Hypoglycemia on Sleep Regulation in Children with Type 1 Diabetes Mellitus" Journal of Sleep Research, 2002, 11 (Suppl. 1), 1-260, 359 O, pp. 1-13.

(Continued)

*Primary Examiner*—Charles A Marmor, II
*Assistant Examiner*—Navin Natnithithadha

(57) ABSTRACT

Method and apparatus for monitoring the sleep state condition of an individual by using an external probe applied to a peripheral body location, such as the individual's finger or toe, for detecting changes in the peripheral vascular bed volume of the individual. A predetermined pressure field is applied to the distal end of the peripheral body location, including its distal-most extremity, to prevent the occurrence of venous pooling within and distal to the peripheral body location. The probe produces an output corresponding to changes in the peripheral arterial bed volume at the peripheral body location, which output provides an indication of the sleep state condition of the individual. Such information is useful in diagnosing and/or in treating, a number of sleep disorders as well as other conditions, such as impotence, diabetes, and various disorders in children.

39 Claims, 12 Drawing Sheets

U.S. PATENT DOCUMENTS

| | | | |
|---|---|---|---|
| 3,920,004 A | 11/1975 | Nakayama | |
| 4,030,485 A | 6/1977 | Warner | |
| 4,112,491 A | 9/1978 | Bugay | |
| 4,406,289 A | 9/1983 | Wesseling et al. | |
| 4,437,470 A | 3/1984 | Prost | |
| 4,515,166 A | 5/1985 | Timm | |
| 4,677,984 A | 7/1987 | Sramek | |
| 4,821,734 A | 4/1989 | Koshino | |
| 4,836,219 A | 6/1989 | Hobson et al. | |
| 4,846,189 A | 7/1989 | Sun | |
| 4,848,361 A | 7/1989 | Penney et al. | |
| 4,862,895 A | 9/1989 | Yamasawa et al. | |
| 4,926,867 A | 5/1990 | Kanda et al. | |
| 5,031,675 A | 7/1991 | Lindgren | |
| 5,065,749 A | 11/1991 | Hasebe et al. | |
| 5,101,831 A | 4/1992 | Koyama et al. | |
| 5,280,791 A | 1/1994 | Lavie | |
| 5,337,744 A | 8/1994 | Branigan | |
| 5,365,924 A | 11/1994 | Erdman | |
| 5,398,682 A | 3/1995 | Lynn | |
| 5,438,986 A | 8/1995 | Disch et al. | |
| 5,542,421 A | 8/1996 | Erdman | |
| 5,605,151 A * | 2/1997 | Lynn | 600/323 |
| 5,891,023 A * | 4/1999 | Lynn | 600/323 |
| 5,917,415 A | 6/1999 | Atlas | |
| 6,115,621 A * | 9/2000 | Chin | 600/323 |
| 6,162,188 A | 12/2000 | Barnea | |
| 6,223,064 B1 * | 4/2001 | Lynn et al. | 600/324 |
| 6,319,205 B1 | 11/2001 | Goor et al. | |
| 6,342,039 B1 * | 1/2002 | Lynn et al. | 600/529 |
| 6,343,223 B1 * | 1/2002 | Chin et al. | 600/323 |
| 6,748,252 B2 * | 6/2004 | Lynn et al. | 600/323 |
| 6,760,608 B2 * | 7/2004 | Lynn | 600/324 |

FOREIGN PATENT DOCUMENTS

| | | |
|---|---|---|
| WO | WO 9804182 A2 * | 2/1998 |
| WO | WO 98/04182 | 5/1998 |
| WO | WO 99/63884 A1 | 12/1999 |
| WO | WO 01/64101 A1 | 9/2001 |
| WO | WO 02/073948 A2 | 9/2002 |
| WO | WO 02/080752 A2 | 10/2002 |

OTHER PUBLICATIONS

Raymond et al., Combined Index of Heart Rate Variability and Oximetry in Screening for the Sleep Apnoea/Hypopnoea Syndrome, J. Sleep Res. (2003), 12, 53-61.

* cited by examiner

METHOD AND APPARATUS FOR THE NON-INVASIVE DETECTION OF PARTICULAR SLEEP-STATE CONDITIONS BY MONITORING THE PERIPHERAL VASCULAR SYSTEM

RELATED APPLICATIONS

This application is a Continuation-in-Part of International Application PCT/IL01/00199 filed Mar. 1, 2001, published as WO 01/64101 on Sept. 7, 2001. This application also includes subject matter, and also claims the priority dates, of U.S. Provisional Application 60/305,197 filed Jul. 16, 2001, U.S. Provisional Application 60/368,136 filed Mar. 29, 2002, the contents of which Provisional Applications are incorporated herein by reference in their entireties. PCT Application PCT/IL01/00199 claims the benefit of U.S. Provisional Application 60/240,079 filed Oct. 16, 2000, U.S. Provisional Application 60/212,648 filed Jun. 19, 2000 and U.S. Provisional Application 60/186,358 filed Mar. 2, 2000.

FIELD AND BACKGROUND OF THE INVENTION

The present invention relates to a method and apparatus for the non-invasive detection of certain medical conditions, particularly certain sleep-state conditions, in an individual by monitoring the peripheral vascular system of the individual. The invention also relates to methods and apparatus for aiding in diagnosing the cause of a functional impotence condition, the cause of abrupt changes in the nocturnal glucose level of a diabetic patient, and/or other disorders or conditions in the individual.

PCT Applications No. PCT/IL97/00249 published Feb. 5, 1998 (International Publication No. WO 98/04182); No. PCT/IL99/00292 published Dec. 16, 1999 (WO 99/63884), No. PCT/IL00/00307 published Dec. 14, 2000 (International Publication No. WO 00/74551), No. PCT/IL00/00403 published Jan. 18, 2001 (WO 01/03569), all of which are hereby incorporated by reference as if fully set forth herein, describe non-invasive devices for measuring blood pressure and for detecting various medical conditions, including: myocardial ischemia, certain sleep state conditions, endothelial dysfunction (ED), and stress-induced myocardial ischemia. In the preferred embodiments described in those applications, the described non-invasive devices used volume-measuring sensors and optical sensors for measuring changes in the peripheral arterial bed volume of the individual, which changes were translated to changes in the peripheral arterial tone.

The present application is directed to detecting certain sleep-state conditions, particularly sleep disordered breathing in an individual.

The broad area of sleep disordered breathing encompasses a number of recognized abnormal conditions, including: the obstructive and central sleep apnea syndrome, which results in complete cessations of breathing that occur repeatedly during sleep; obstructive hypopneas, which results in partial upper airway obstruction and reduced ventilation; and the upper airway resistance syndrome (UARS), which results in subtle respiratory changes even though the airflow may appear to be normal. All the foregoing conditions produce frequent awakenings and sleep fragmentation which result in impaired sleep quality and daytime functioning.

Even with the comprehensive battery of measurements used in laboratory based polysomnographic evaluations, the diagnosis of UARS is extremely problematical due to the difficulty in visibly scoring the subtle respiratory changes. [Guilleminault C, Stoohs R, Clark A, Cetel M and Maistros P, "A Cause of Excessive Daytime Sleepiness. The Upper Airway Resistance Syndrome", Chest 104:781-787 (1993)]. A proper diagnosis of this syndrome necessitates the insertion of an esophageal balloon to measure the patient's intra-thoracic pressure changes. This technique causes great inconvenience and is not well tolerated.

A possible measurable parameter for aiding in the diagnosis of UARS may be the occurrence of frequent cortical or autonomic arousals during sleep. This may be marked by bursts of changes in the electro-encephalographic (EEG) activity, or by bursts of increased sympathetic activation. In many cases, however, there is only increased sympathetic activity with no evidence, or insufficient evidence of cortical arousal in the EEG.

A simple and robust method and apparatus, capable of being used outside the confines of the sleep laboratory for monitoring the sleep state condition, and particularly for marking arousals, would be a very important diagnostic tool in the identification of what might otherwise be an unrecognizable disease state, or in determining the cause of a detected disorder. An example of the latter application described below is in diagnosing the cause of a functional impotence condition in an adult male. Another example described below is in diagnosing and/or treating diabetic conditions of children as well as adults. Further examples are described below particularly applicable to children.

With respect to the impotence application, impotence is the inability of a male to produce or maintain a penile erection such as to enable the male to have sexual intercourse. The condition may stem from organic causes or psychogenic causes. The treatment, therefore, depends to a great extent on the cause. For example, organic causes, such as a small or deformed penis, can frequently be corrected by surgery, whereas other organic causes, such as disease or other disorders, generally require treatment of the disease or disorder causing the condition. On the other hand, where the impotence has a psychogenic basis, the treatment may require the services of a sex therapist or a marriage counselor.

Penile erection, or the lack thereof, during periods of REM sleep have been used to determine whether a patient's impotence may be of an organic or a psychogenic cause. Thus, it has been found that during sleep, normal fluctuations in the autonomic nervous system, which regulates blood flow to the penis, result in periodic, transient penile erections. Such nocturnal erections are substantially unaffected by an erectile dysfunction of a psychogenic origin, but are affected by such a dysfunction which is of an organic nature. A number of penile tumescence and rigidity monitoring devices have been developed and are available for monitoring nocturnal penile erections, as described, for example, in U.S. Pat. Nos. 6,162,188; 4,848,361 and 4,515,166, the contents of which are incorporated herein by reference.

With respect to applications for diagnosing or treating diabetic conditions, it is well known that the risk of hypoglycemia is greater during sleep than during wakefulness. Although the mechanisms underlying this increased risk are unclear, it appears they may be related to blunted counter-regulatory hormonal responses during sleep.

The continuous subcutaneous glucose sensor has been shown to measure glucose levels accurately without causing sleep disruption and allows sampling every five minutes. The subcutaneous continuous glucose determination is however an invasive measurement that requires the surgical insertion of the sensor into the subcutaneous fat of the patient's abdomen. This process is uncomfortable and carries some potential risk. As will be described more particularly below, the novel method and apparatus of the present invention may be used as a non-invasive technique to determine if a diabetic patient is experiencing rapidly changing blood glucose levels during sleep and thereby facilitate the detection of hypoglycemia in diabetic patients during sleep, provided that the patient does not suffer from a concomitant sleep disordered breathing disorder.

BRIEF SUMMARY OF THE PRESENT INVENTION

According to one aspect of the present invention, there is provided a method of monitoring an individual for the occurrence of a particular condition during the sleep state of the individual, comprising: applying an external probe to an external surface at a peripheral location on the individual's body for monitoring the peripheral vascular bed volume of the individual at the peripheral body location while applying a predetermined pressure field to the distal end of the peripheral body location, including its distal-most extremity, effective to prevent the occurrence of venous pooling within the peripheral body location, and thereby to produce an output from the probe corresponding to changes in the peripheral arterial bed volume at the peripheral body location; while the individual is in a sleep state, utilizing the probe to detect: (a) changes in the peripheral vascular bed volume of the individual at the peripheral body location, (b) amplitude changes in the probe output or changes in the time course of the response pattern of the probe output, and (c) changes in the individual's pulse rate and amplitude, and to produce outputs corresponding to such changes; and determining the sleep state condition of the individual according to such changes detected by the external probe.

Preferably, the external probe used is one of the several non-invasive finger-probes described in the above-cited PCT applications for monitoring the peripheral vascular bed volume of the individual, and for translating the measurements to changes in peripheral arterial tone. Particularly described were volume measuring probes and optical measuring probes applied to a finger (or toe) of the individual. Such probes were found to provide numerous advantages in monitoring the individual's vascular system for changes in the peripheral arterial bed volume, particularly in the following respects:

1) by applying near diastolic pressure over the surface of the finger, which is transmitted to the arteries within the finger, they reduce the transmural pressure within those arteries, thereby freeing the arterial walls of tension and increasing their compliance allowing them to move more freely;

2) by providing such pressure, they are able to prevent the pooling of venous blood in the measured part of the finger, thereby avoiding the occurrence of venous distention and possible reflex arterial constriction as a result of the venous distention;

3) by providing a contiguous buffer region proximal to the measurement site, they are able to reduce the effects of retrograde venous pressure perturbations and to extend the effective boundary of the pressure field in the measurement portion of the probe.

The foregoing features of the finger probes described in the above-cited patent applications have been found to enhance their performance for the many described uses of the probe. While such probes remain the preferred ones due to these advantageous characteristics, it will be appreciated that the invention described below can also be implemented by using other peripheral vascular bed volume monitoring devices for detecting the specific markers to be described below. Examples of other types of devices for monitoring the changes in the peripheral vascular bed volume include: segmental plethysmographs, circumferential strain gage devices, optical plethysmographs, Doppler or laser Doppler sensors, isotope washout devices, thermal washout devices, electromagnetic devices, and any other devices which are affected by a change in the geometry of the finger (or other peripheral body part, e.g. toe or ear-lobe) in response to blood volume changes.

Examples of different sleep state conditions detected in accordance with the invention described below include: arousals during the sleep state, apneas, hypopneas, UARS events, a Cheyne-Stokes breathing pattern, periodic leg movements syndrome (PLMS) and rapid eye movement sleep state (REM).

According to another aspect of the present invention, there is provided a method of producing information helpful in diagnosing the cause of a functional impotence condition in a male patient, comprising: monitoring penile tumescence of the patient while sleeping to detect nocturnal penile erections; monitoring the sleep state condition of the patient while sleeping to detect frequency of awakenings, episodes of apnea, and/or REM sleep stages; and utilizing information obtained by the monitoring operations to aid in determining whether the functional impotence condition in the patient is more likely due to an organic cause or to a psychogenic cause.

According to a still further aspect of the present invention, there is provided a method of indirectly monitoring the functional blood glucose level condition of a diabetic patient, comprising: while the patient is sleeping, monitoring the sleep state condition of the patient; and utilizing the results of the sleep state monitoring operation for indicating the probable occurrence of abrupt changes in the glucose level.

According to yet another aspect of the present invention, there is provided apparatus for monitoring an individual to detect the occurrence of a particular condition during the sleep state of the individual, comprising: an external probe to be applied to an external surface at a peripheral location on the individual's body for monitoring (a) changes in the peripheral vascular bed volume of the individual at the peripheral body location, (b) amplitude changes in the probe output or changes in the time course of the response pattern of the probe output, and (c) changes in the individual's pulse rate and amplitude, and for producing outputs corresponding thereto; the external probe including a pressure applicator for applying a predetermined pressure field to the peripheral body location including its distal-most extremity to reduce venous pooling and thereby to produce an output signal from the probe corresponding to changes in the peripheral arterial bed volume at the peripheral body location; and a processor for processing the outputs from the probe and for producing a signal indicating the particular sleep state condition when a predetermined change in the output of the probe is detected.

According to a still further aspect of the present invention, there is provided apparatus for producing information helpful in diagnosing the cause of a functional impotence condition in a male patient, comprising: a penile tumescence monitoring device for monitoring penile tumescence of the patient while sleeping to detect nocturnal penile erections, and for producing an output corresponding to the detected nocturnal penile erections; a sleep state monitoring device for monitoring the sleep state condition of the patient while sleeping to detect frequency of awakenings, episodes of apnea, and/or REM (rapid eye movement) sleep stages, and for producing an output corresponding to the detected sleep state condition; and a processor for receiving and processing the outputs of the monitoring devices, and for producing an output indicative of detected nocturnal penile erections with respect to the detected sleep state condition to aid in determining whether the functional impotence condition in the patient is more likely due to an organic cause or to a psychogenic cause.

According to a still further aspect of the present invention, there is provided apparatus for monitoring the glucose level condition of a diabetic patient, comprising: a sleep state monitoring device for monitoring the sleep state condition of the patient while sleeping, and for producing an output corresponding thereto; and a processor for receiving and processing the output of said monitoring device, and for producing an output indicating the probable occurrence of abrupt changes in the measured nocturnal glucose level of the patient.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
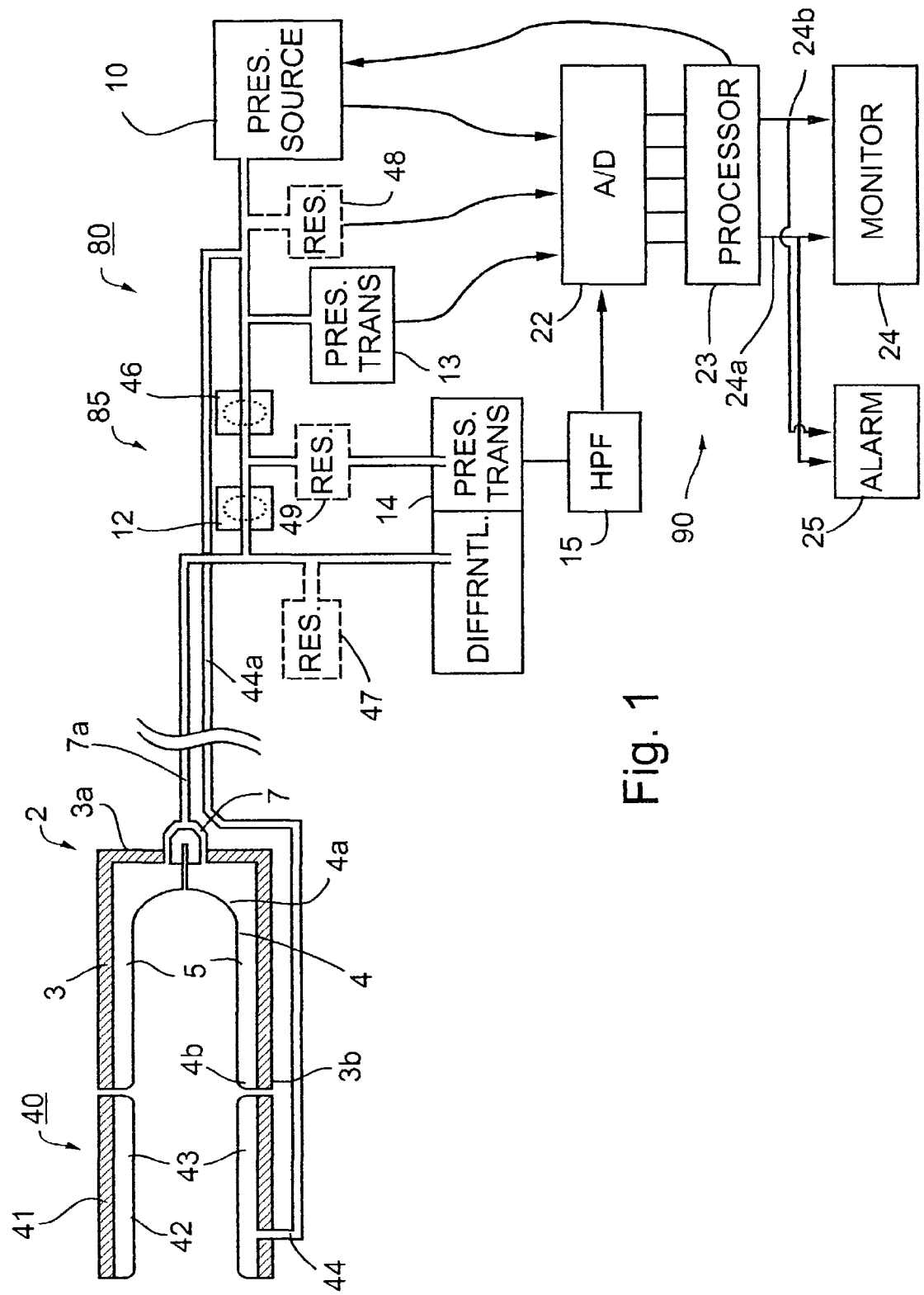
FIG. 1 illustrates one form of apparatus, as described in the above-cited PCT applications, that may be used to implement the present invention as described below.
Figure 2:
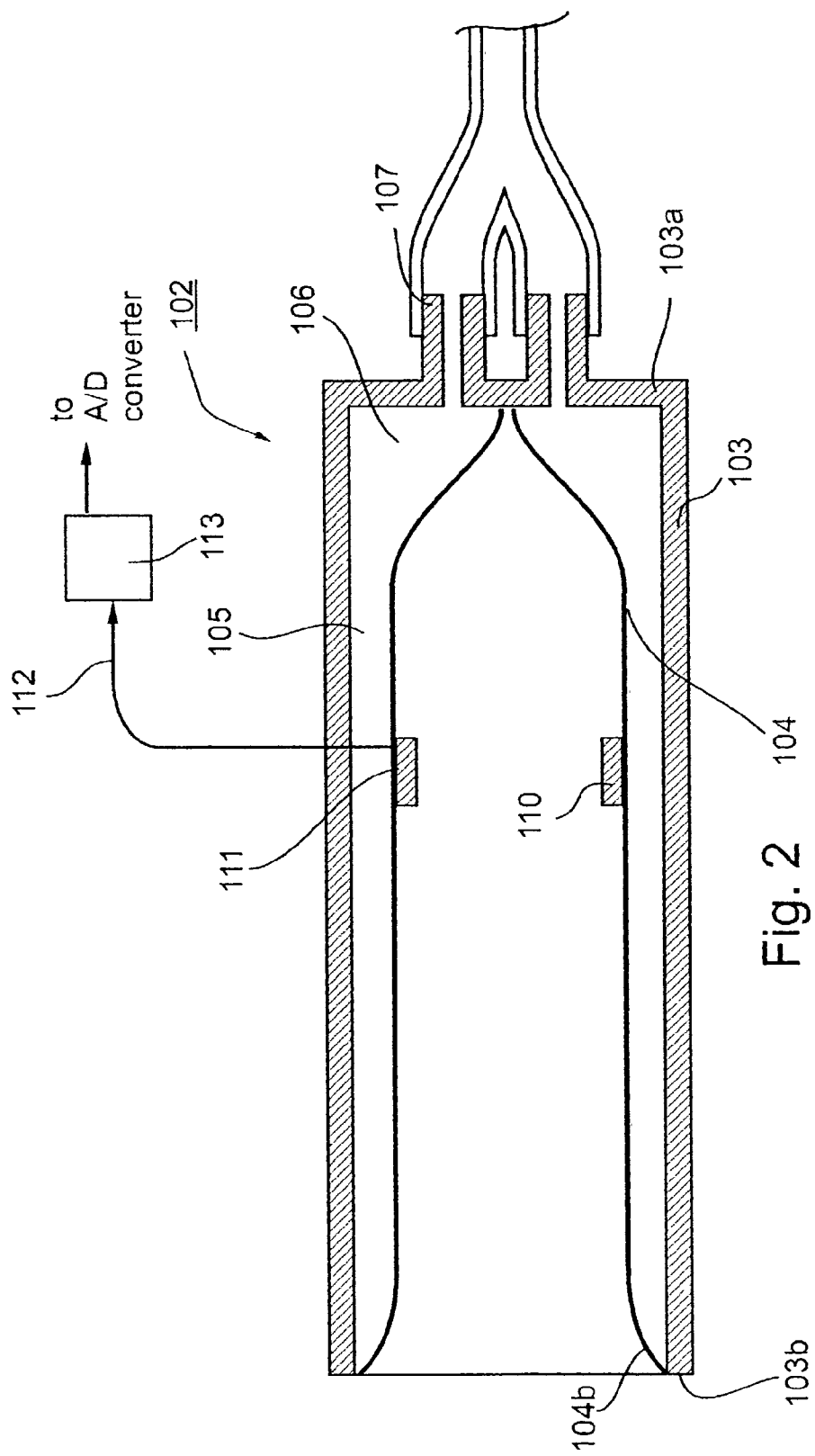
FIG. 2 illustrates another finger-probe, including an optical sensor, which may be used in the apparatus of FIG. 1.

The Finger Probe Construction FIGS. 1 and 2

Figure 9:
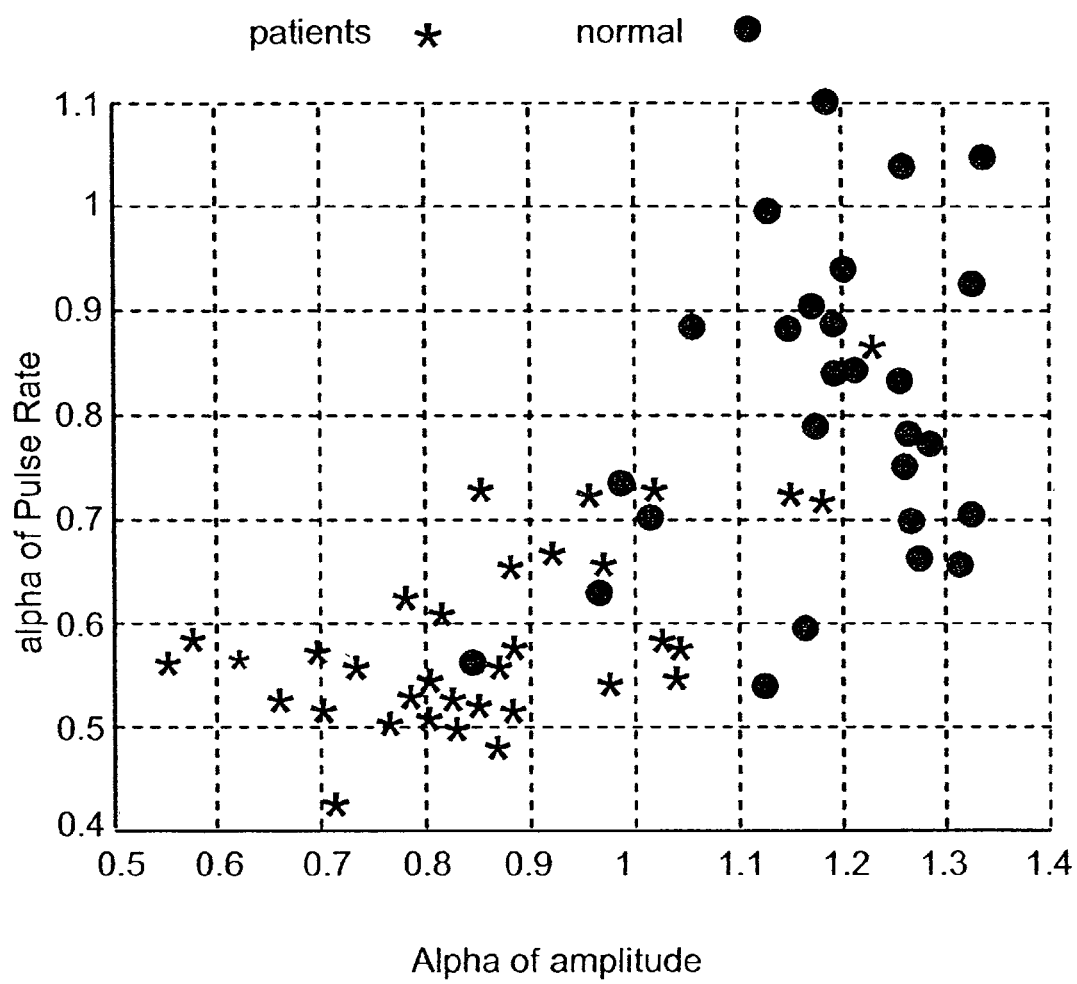
FIG. 9 is a scattergraph showing how the finger-probe output can be used in the known Detrended Fluctuation Analysis (DFA) method for the detection of congestive heart failure (CHF)

FIG. 1 illustrates a finger probe, therein generally designated 2, of the construction described in the above-cited U.S. Pat. No. 6,319,205 (FIG. 9). For the sake of brevity, only the main parts of such a probe are illustrated in FIG. 1 and are described below. However, for the sake of completeness, the entire contents of the above-cited U.S. Patent are incorporated herein by reference, to provide further particulars as to the construction and operation of such a probe.

The finger probe illustrated in FIG. 1 and therein generally designated 2, is applied to the finger or toe of the patient for detecting changes in the peripheral vascular system of the patient, more particularly, changes in the peripheral arterial tone in the patients finger or toe while the patient is sleeping. It includes a pressure applicator for applying a near diastolic pressure over the surface of the finger or toe to reduce the transmural pressure within the arteries in the finger or toe, thereby freeing the arterial walls of tension and preventing pooling of venous blood in the finger or toe. The pressure applicator also extends the pressure field to the distal end of the finger or toe and thus provides a contiguous buffer region proximate to the detector site. In the finger probe illustrated in FIG. 1, the pressure applicator is supplied from an external fluid pressure system.

More particularly, finger probe 2 illustrated in FIG. 1 includes a rigid tubular casing 3 in the form of a thimble-shaped end cap, closed at one end 3a and open at the opposite end 3b for receiving a patient's finger. A deformable membrane 4 of tubular configuration is located within end cap 3 and is similarly closed at one end 4a and open at the opposite end 4b. Membrane 4 is of a diameter to define a socket for receiving the end of the person's finger, and to produce between the membrane and the inner surface of casing 3, a closed tubular chamber 5 which expands and contracts depending on the pressure inside the chamber. Chamber 5 is connected via a port 7 and a tube 7a to a pressurized fluid source 10, such as a source of pressurized air.

The pressure from source 10 is controlled by a valve 12 and is measured by a pressure transducer 13 upstream of the valve. The differential pressure on the opposite sides of valve 12 is measured by a differential pressure transducer 14. A high pass filter 15 filters the output of transducer 14 before applying same to an analogue-to-digital converter 22, together with the output of pressure transducer 13. The analogue-to-digital converter 22 feeds its output to a processor 23 which produces outputs 24a, 24b, to a monitor circuit 24 and also to an alarm circuit 25.

Probe 2 illustrated in FIG. 1 further includes a pressure cuff 40 constituted of a rigid cylinder 41 and a membrane 42 defining a chamber 43 which can be pressurized via an inlet 44 communicating via a tube 44a with the pressurized source 10. Another valve 46 is provided upstream of the differential pressure transducer 14 to enable measuring the differential pressure across valve 12. Reservoirs 47, 48 and 49, shown in FIG. 1 within broken lines to indicate that such reservoirs are optional, may be provided to decrease the sensitivity of volume changes in the respective chambers to small volume losses of gas due to leaks or to elasticity of the respective conduit system, and also to reduce the size of the back pressure changes due to the pulse waves.

In order to perform a diagnostic procedure, valves 12 and 46 are first opened, and the chambers 5 and 43 of the finger-probe are evacuated to allow the patient to insert a finger into the probe. Then, the pressure is raised to a near diastolic pressure, sufficient to unload the arterial walls and to prevent venous pooling. The pressure applied by source 10 is measured by pressure transducer 13 upstream of valves 12 and 46. In the preferred embodiment, the pressure in the pneumatic compartments is automatically raised to 70 mm Hg.

At this point, valves 12 and 46 are closed, so that the pressure in the right chamber of pressure differential transducer 14 is kept constant. On the other hand, the pressure in the left chamber of transducer 14 varies depending on the pressure inside chamber 5 of the finger-probe 2.

Changes in the volume of the subject's finger which are due to arterial blood pressure pulse waves produce an expansion or contraction of chamber 5, and a corresponding decrease or increase in the gas pressure within chamber 5. Since valve 12 is closed, the pressure changes affect only the left chamber of differential-pressure sensor 14. The differential pressure sensor 14 detects these pressure changes and provides an output corresponding to the pressure changes.

A/D converter 22 receives the analog outputs of pressure transducers 13 and 14, and converts them into digital form before introducing them into CPU processor 23. Processor 23 processes the measured finger volume changes to produce output 24a of the volume measurements, and/or output 24b of the volume change measurements with respect to time. Either one or both measurements can be displayed on the monitor 24 as well as recorded in a memory.

If the displayed output 24 shows a change in the measured volume, indicating peripheral vasoconstriction, this will be immediately seen by the observer viewing monitor 24.

The peak to trough amplitude of the signal is generally proportional to the arterial pulsatile volume changes, and will decrease or attenuate upon peripheral vasoconstriction. Therefore, when the system of FIG. 1 is used for detecting peripheral vasoconstriction, the observer would be interested in relative changes of the amplitude of the trough to peak values, as opposed to the absolute values of the pressure.

The annular pressure cuff 40 is coaxial with and contiguous to the end cap 3, on the proximal (heart) side of the device. The main purpose of the pressure cuff is to extend the boundary of the constant pressure field beyond the borders of the sensing probe, so as to avoid edge effects. Chamber 43 of the pressure cuff is also filled with a pressurized gas via conduit 44; however, solenoid valve 46 isolates conduit 44 from transducer 14. Cuff 40 thus extends the static pressure field for a distance in the proximal (heart) direction from the site of measurement of the finger volume changes accompanying blood pressure waves. The annular pressure cuff 40 acts as a venous tourniquet which, together with the pressure field produced in end cap 3, prevents venous pooling in the distal end (particularly the most distal phalange) of the finger. It also substantially prevents uncontrolled venous back flow. Further, it partially unloads the wall tension of, but does not occlude, the arteries in the distal end of the finger when the finger is at heart level. While the pressure in the pressure cuff may differ from that in the sensing chambers 5, it should not exceed it.

Further details of the construction and operation of the finger probe 2 illustrated in FIG. 1, and particularly the manner in which it may be used to detect various sleep state conditions of the patient including frequency of awakenings, episodes of apnea, and REM sleep stages, are described in the above-cited U.S. Pat. No. 6,319,205.

FIG. 2 illustrates another finger probe, also described in U.S. Pat. No. 6,319,205, similar to that of FIG. 1 except that changes in the optical density are sensed and measured, rather than changes in volume, to provide a measurement of changes in the peripheral vascular system, and thereby an indication of the sleep state condition of the patient while sleeping.

Thus, the finger probe illustrated in FIG. 2, therein generally designated 102, also includes a rigid housing 103 closed at one end 103a and open at the opposite end 103b, receiving a tubular membrane 104 also closed at one end 104a and open at the opposite end 104b. End 104b of the membrane is in contact with the open end 103b of the casing to define a fluid chamber 105 between the two. Chamber 105 is connected via a port 107 formed in the casing end wall 103a to a pressurized fluid source (not shown), as described above with respect to FIG. 1.

Probe 102 illustrated in FIG. 2 measures changes in the finger by an optical device including a light source 110 to be located on one side of the finger, and a light receiver or detector 111 to be located on the opposite side of the finger, such that pulsatile blood volume changes in the finger are detected as changes in optical density by the light detector 111. This information is fed via conductors 112 to an amplifier 113, where the information is amplified and filtered, before being fed to the A/D converter (22, FIG. 1) for processing by the processor (23, FIG. 1), as described above.

In the probe illustrated in FIG. 2, the measurement site, namely the location of the light source 110 and light detector 111, is considerably inwardly of the open end of the rigid casing 103 of the probe 102 which applies the static pressure field uniformly around the outer end of the finger. Therefore the annular pressure cuff (40, FIG. 1) need not be included. However, if it is desired to locate the light source and light detector closer to the open end of the rigid casing of the probe 102, the annular pressure cuff (corresponding to pressure cuff 40 in FIG. 1), may also be used in the probe illustrated in FIG. 2.

Further details of such probe construction and various modifications thereof, as well as methods of using the probe for detecting sleep state conditions of a patient, and for diagnosing various other medical conditions, are described in the above-cited U.S. Pat. No. 6,319,205 incorporated herein by reference.

Monitoring Various Sleep State Conditions (FIGS. 3-10)

While the descriptions in the above-cited U.S. Pat. No. 6,319,205 focus mainly on measuring blood pressure and detecting myocardial ischemia, the method and apparatus of the present invention are directed primarily to monitoring various sleeping conditions of a subject, particularly the rapid eye movement (REM) sleep stage, sleep arousals, sleep apnea, sleep hypopnea, upper airways resistance, periodic leg movement syndrome, Cheyne-Stokes breathing, and congestive heart failure.

Sleep staging, in particular the determination of REM (Rapid Eye Movement) stage sleep, is a vital tool for diagnosing sleep disorders and numerous other conditions. During REM sleep, altered control of breathing occurs with greatly reduced chemosensitivity resulting in highly irregular breathing patterns and the greatest declines in blood oxygen saturation.

Changes in REM latency have been reported in a plethora of affective illnesses including endogenous depression, schizophrenia, anxiety disorders, obsessive-compulsive disorders, eating disorders as well as in narcolepsy, alcoholism, Alzheimer's disease and impotence. REM latency is important not only in the diagnosis of these conditions but also in therapy and follow up since it is a sensitive indicator of the patient's condition.

A robust association was found between REM stage sleep and the attenuation of the finger-probe output signal. This attenuation was of a substantial magnitude compared to the prior non REM period. Three representative examples showing the time-course of the probe-output signal and sleep hypnograms were shown in FIG. 21 of U.S. Pat. No. 6,310,205. It is important to note that the attenuation of the finger-probe output signal amplitude was not triggered by REM sleep, but appeared to be related to an ongoing cycle that was synchronized with the sleep stages cycle in such a way that the nadirs of this cycle coincided with REM sleep.

Currently, REM stage sleep is identified by polysomnography, which requires costly apparatus, considerable patient instrumentation and specialized staff. One simplified REM detector is the "night cap" disclosed in U.S. Pat. No. 4,836,219 to Hobson et al. which relies on two channels of information to detect REM sleep; body movements and eye movements. However, this method requires substantial instrumentation which may be uncomfortable for the patient and detrimental to sleep. Another patented device (U.S. Pat. No. 5,280,791 to Lavie) employs a heart rate variability method. However, this method requires demanding signal analysis, and may not be as reliable as the method utilizing the output signal of the finger-probe.

REM detection utilizing the above-described probe could be an extremely useful adjunct to existing ambulatory monitoring systems, since it yields important information with a minimum of patient instrumentation in a highly cost effective manner. It could be used to provide intensive, long term, follow up in the patient's own home, which would be a logistic impossibility in the sleep lab setting. The probe could be readily used in combination with oxygen saturation monitoring and ambulatory apnea screening. It could eliminate the need for subjective operator evaluation of sleep studies and the dependency on the specialized and expensive instruments needed for laboratory based sleep staging, such as EEG, EOG and EMG measurements.

Figure 3:
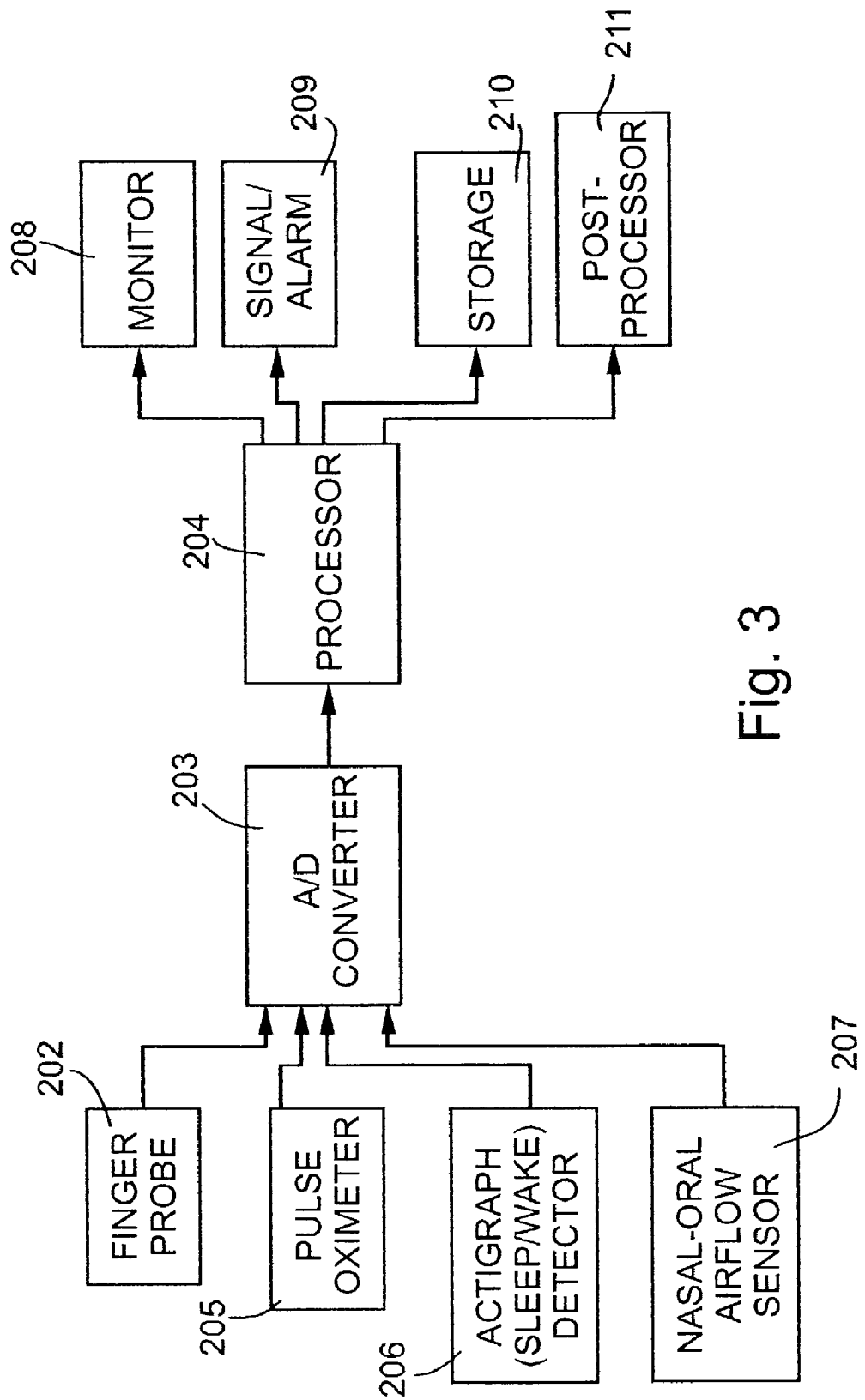
FIG. 3 is a block diagram illustrating one form of overall system constructed in accordance with the present invention particularly useful for monitoring various conditions during the sleep state of the individual.

FIG. 3 illustrates an example of a set-up which may be used for performing these tests. In this illustrated set-up, the finger-probe 202 (e.g., of the construction described above in FIG. 1 or FIG. 2) provides one input, via an analog-digital converter 203, to a processor 204. The processor 204 includes additional inputs from a pulse oximeter 205, which measures the oxygen saturation level of the blood; from an actigraph 206, which serves as a sleep/wake detector; and from a nasal-oral airflow sensor 207, such as a thermistor, which measures the nasal-oral air flow of the sleeping patient; and from at least a single electrocardiograph electrode dipole for registering the patient's ECG.

The foregoing inputs are processed by processor 204, which produces outputs to a monitor 208, a signal and/or alarm unit 209, a storage device 210, a post-processor device 211.

Figure 4:
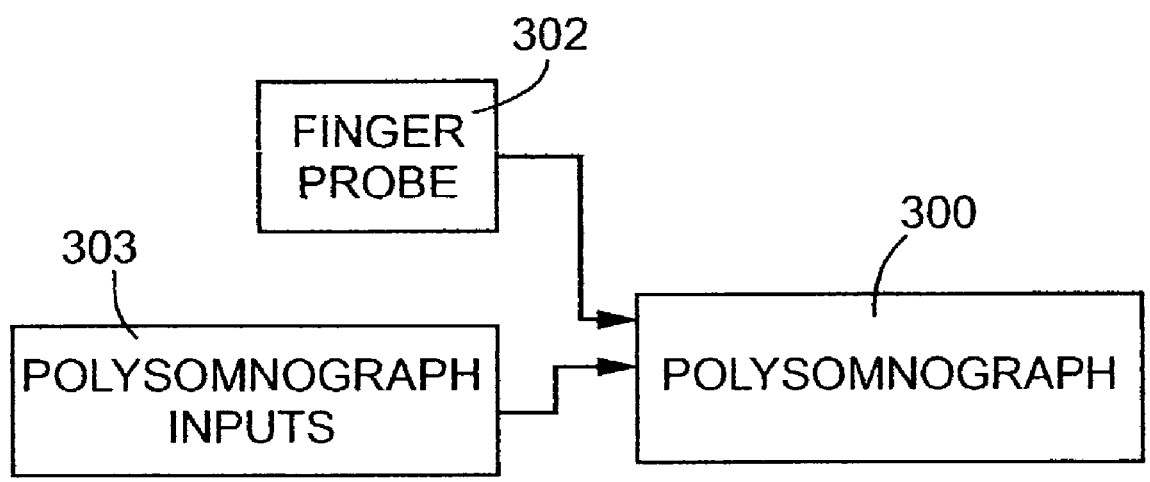
FIG. 4 is a block diagram illustrating the incorporation of a finger-probe in accordance with the present invention as one input in a known polysomnograph system.

FIG. 4 illustrates another set-up including a conventional polysomnograph 300, which includes the output from the finger-probe 302 as one of the inputs, together with the other inputs 303 commonly provided in such apparatus.

During numerous highly controlled sleep studies in elite sleep laboratories, it was also found that there was a highly robust association between the appearance of alpha wave encephalographic activity signifying awakening during sleep, and attenuation of the finger-probe signal. This attenuation was of a substantial magnitude and was tightly linked to the appearance of the alpha wave activity, with a consistent time delay between the two phenomena.

Figure 5:
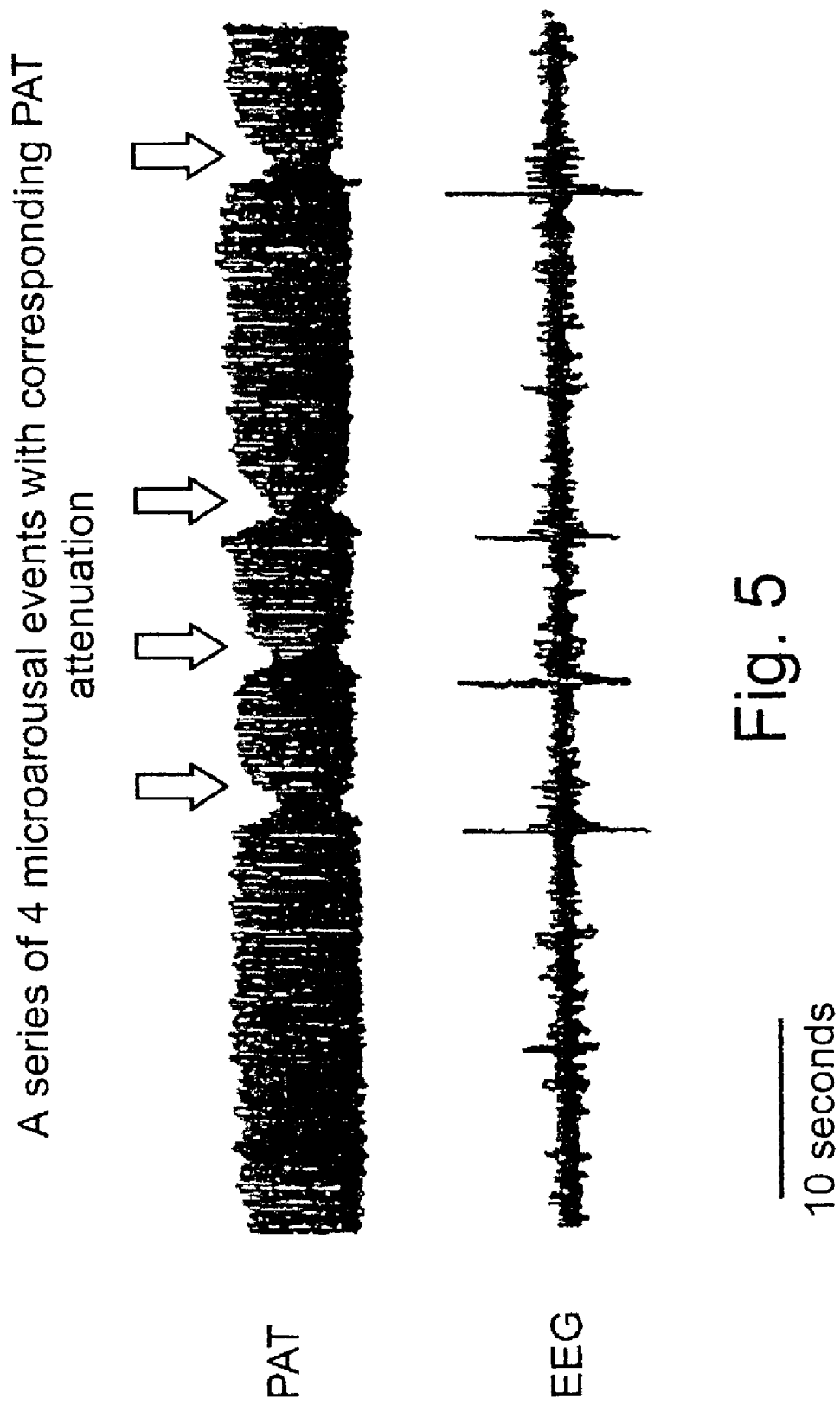
FIG. 5 is illustrates the finger-probe output waveform of a sleeping individual compared to the individual's EEG waveform showing sleep arousals.

A representative example showing the time-course of the finger-probe signal and the patient's EEG signal associated with such alpha wave activity is shown in FIG. 5 illustrating a compressed record of a series of K-alpha events. These are typical microarousals, each comprised of a K complex with a tail of alpha EEG activity. These events are the hallmark of the upper airway resistance syndrome (UARS) and may therefore be used for detecting UARS.

It is important to note that the maximum attenuation of the finger-probe signal amplitude always occurred after the appearance of the alpha wave. The finger-probe signal may therefore also be used for detecting UARS.

Figure 6:
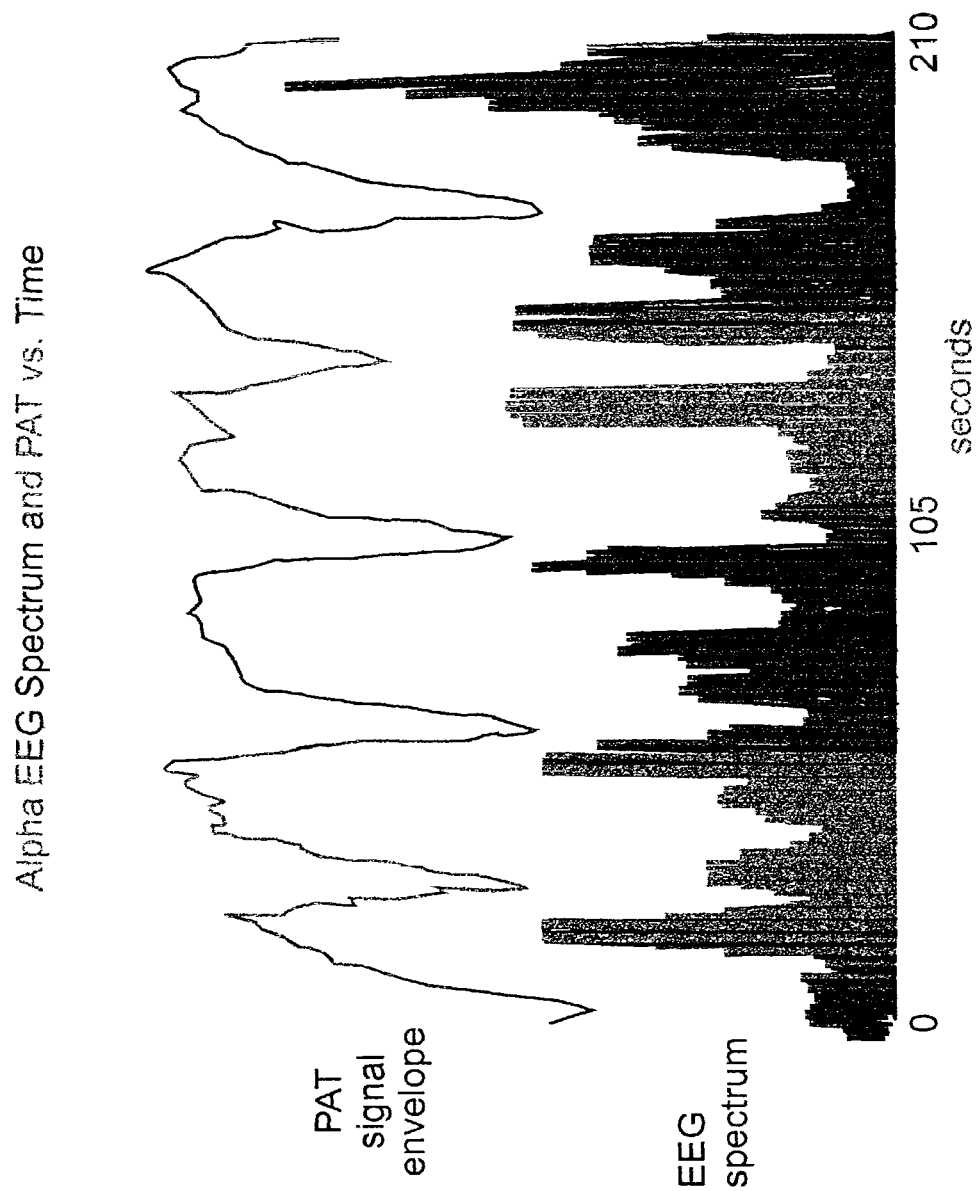
FIG. 6 illustrates the finger-probe output waveform of a sleeping individual compared to the individual's EEG spectrum, also showing sleep arousals.

The same strong temporal linkage is clearly seen in the spectrum of the EEG signal which can also be considered as a marker of the alpha activity. This is shown in FIG. 6 wherein the upper waveform is the finger-probe output signal envelope, and the lower waveform is the EEG spectrum of the sleeping individual.

In addition to the highly consistent linkage between alpha activity and finger-probe output over time, it was found the attenuation of the finger-probe output reached its nadir (trough) several milliseconds after the peak alpha activity Thus, alpha activity leads the nadir attenuation. This delay has been consistently found in a large number of patients and normals and therefore can also be used as an indication of UARS.

An additional finding of diagnostic significance is that it is possible to distinguish between arousals related to the periodic leg movement syndrome (PLMS) and arousals related to disordered breathing events during sleep on the basis of the time interval between probe signal attenuation events. For example, the average time interval between probe signal attenuation events in PLMS is 24.8 seconds while respiratory related attenuation events related to hypopneas had a mean interval of 34.1 seconds. Based on the interval between attenuations it is possible to distinguish between the non-respiratory and respiratory related events with a very high degree of sensitivity of about 85%.

Brief arousal detection by the finger probe could be an extremely useful adjunct to existing ambulatory monitoring systems, since it yields important information with a minimum of patient instrumentation in a highly cost effective manner. Furthermore, adding the finger-probe signal to existing sleep laboratory recordings can aid in the rapid identification of brief arotisals. Such a probe could also be used to provide intensive, long term, follow up in the patient's own home, as well as a means for assessing treatment effectiveness, which would be a logistic impossibility in the sleep lab setting.

Adding the probe to provide an input to the polysomnograph apparatus, as illustrated in FIG. 3 or 4, enables the probe to be readily used in combination with respiratory indices currently used for apnea screening, such as oro-nasal airflow and pulse oximetry. Such apparatus would better enable a differential diagnosis to be made between arousals related to obstructive sleep disordered breathing, non-obstructive sleep disordered breathing disorders, or arousal from sleep such as those occurring in the periodic leg movement syndrome (PLMS). Generally speaking, such a probe would enable UARS, and the other respiratory and non-respiratory conditions which are associated with arousal, to be identifiable both under the sleep laboratory environment, as well as under circumstances in which contemporary sleep apnea ambulatory screening methods would be unable to detect the condition. Also, the conventional arousals scoring which is EEG based, is insensitive to non-cortical arousals and suffers from large inter and intra scorers variability. The analysis of the suggested add on signal to the polysomnography, can be readily done automatically with no such variabilities and, as mentioned before, can add the detection of arousals having non-cortical indices.

In addition to the above described sleep related breathing disorders, there exists a different class of breathing disorders which are not obstructive in nature but which are in fact related to aberrant central nervous system control of breathing during sleep. The phase relationship between the probe output and the alpha waves, as well as the phase relationship between the probe output and the variations in oxygen saturation, can provide important information about the type of the apnea as well as the associated hemodynamic changes.

Figure 7:
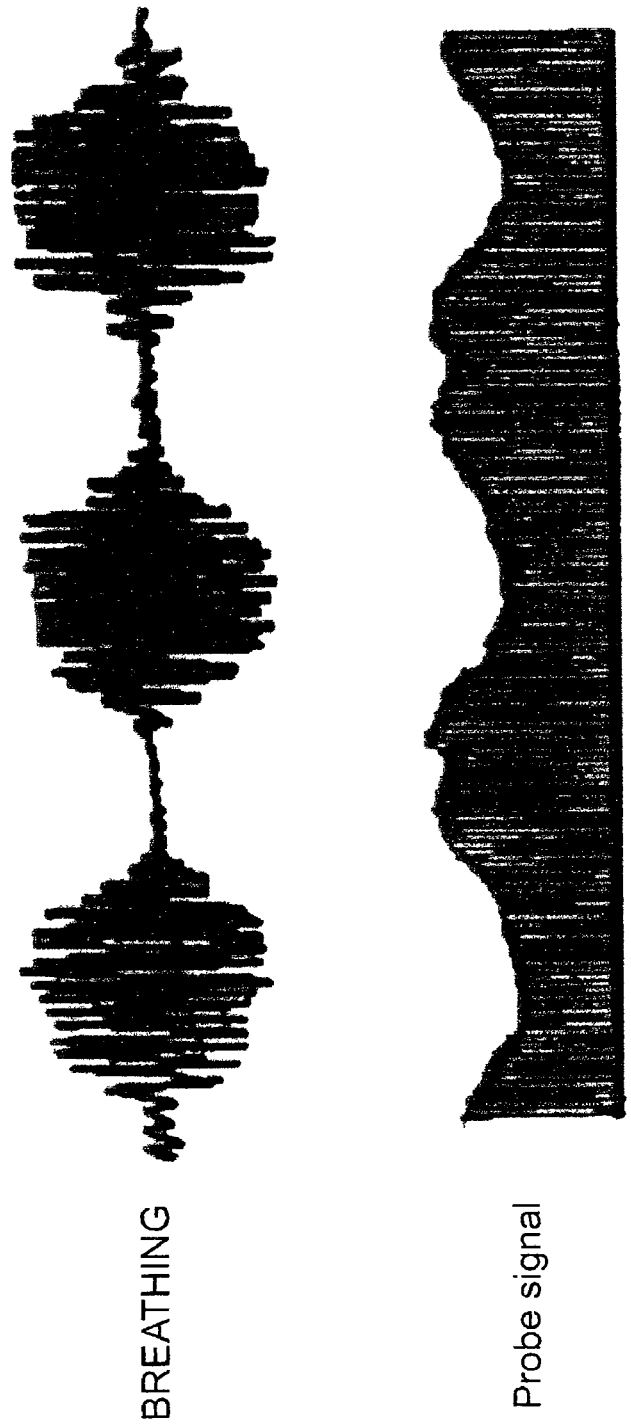
FIG. 7 illustrates the finger-probe output waveform of a sleeping individual compared to the individual's breathing pattern showing Cheyne-Stokes breathing.

For example a characteristic intermittent breathing pattern, known as "Cheyne-Stokes breathing", occurs in patients suffering from advanced congestive heart failure. In this condition the patients breathing is remarkable in that it consists of alternating crescendo and decrescendo patterns of breathing. The existence of this breathing pattern can be detected by the described finger-probe since a remarkable concordance has been found to exist between the periodic breathing and periodic changes in the amplitude of the finger-probe signal. An example of this is shown in FIG. 7.

It was also found that when the probe output signal, and the oxygen saturation level of the blood, are considered in this condition, the nadirs of the probe output signal coincide with nadirs of blood oxygen saturation levels in some individuals, while it coincides with peak values in others. These differences may be related to cyclic activation of sympathetic nervous activity in response to the accumulating respiratory debt. The probe output signal begins to attenuate at the start of the respiratory crescendo phase in some cases, whereas in other cases, the probe output signal may only begin to increase in amplitude with the onset of the crescendo breathing phase, possibly related to improving cardiac function with the improvement of ventilation.

The probe output signal has also been found to be a highly effective in detecting disordered breathing in sleep based on the circulatory responses to what is primarily a condition of disordered breathing. For example, it is known that apneas terminate in brief arousals, which are associated with tachycardia and elevated blood pressure suggestive of sympathetic activation (Morgan, Crabtree, Puleo. et al., 1996; Pitson and Stradling, 1998).

Thus, using the probe for monitoring the pulse wave in patients with full-blown sleep apnea syndrome revealed that terminations of the apneas are associated with marked attenuation of the pulse wave amplitude and usually with evidence of an increase in pulse rate. The attenuations coincided with the rebreathing phase, maintaining a constant phase relationship with the associated electroencepalographic waking activity. It was found that maximal vasoconstriction was delayed by approximately 7 seconds with respect to the first sign of arousal.

In about 10% of the patients with severe sleep apnea syndrome, using the finger-probe for monitoring the pulse wave during sleep revealed a different picture. In addition to the arousal-related attenuation in the probe output, in these patients the probe output was also profoundly attenuated during the initial stages of the apnea.

Figure 8A:
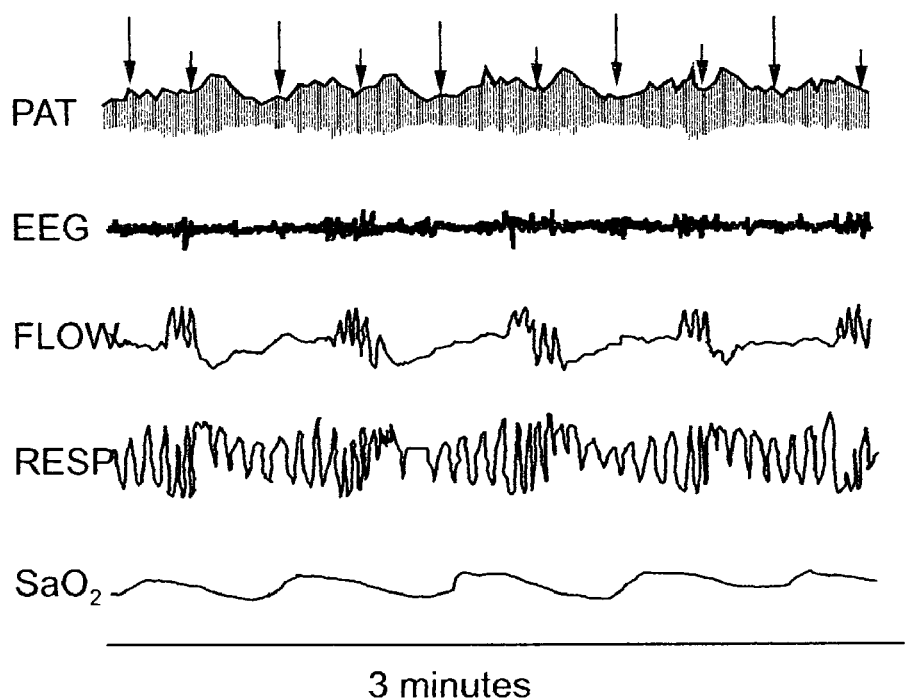
FIGS. 8a and 8b illustrate the finger-probe output waveforms of a sleeping individual compared to other sensor waveforms of the individual showing both apnea events and sleep arousals.
Figure 8B:
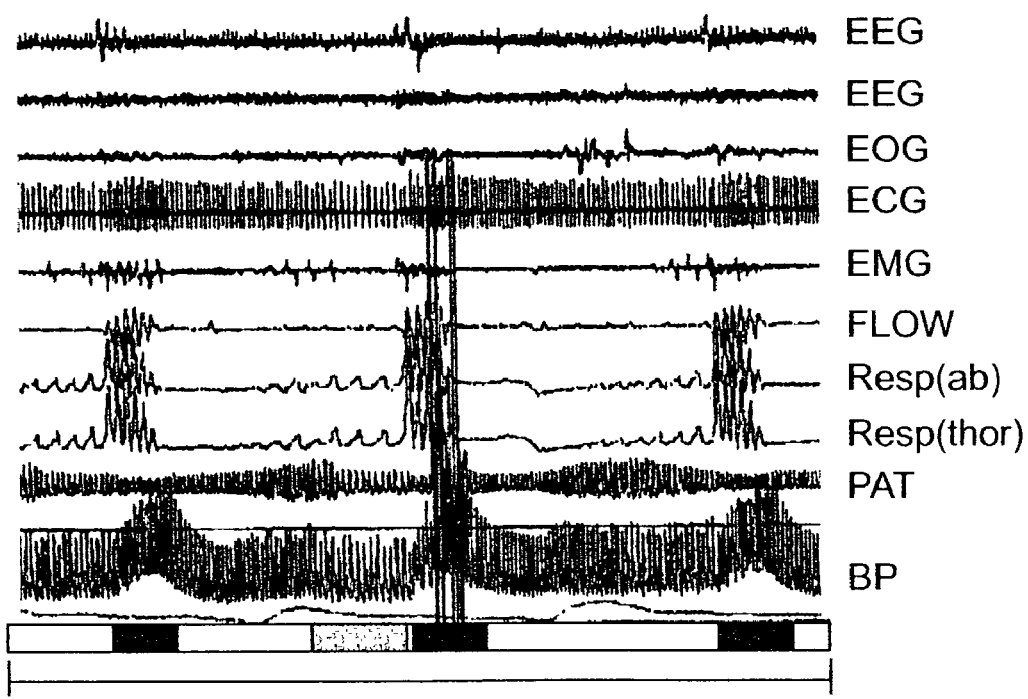

This is exemplified in FIGS. 8a and 8b showing that each apnea was associated with two attenuations rather than with one: the first was associated with the onset of the apnea, and the second with the arousal response at the end of the apnea.

In FIG. 8a, the large arrows indicate periods of the probe signal attenuation associated with the apneic periods. The smaller arrows indicate attenuations in the probe amplitude associated with brief arousal which are also associated with renewal of airflow and increased pulse rate. This can be clearly seen in the ECG tracing in FIG. 8b where the distance between the individual ECG signals is noticeably smaller. Similar changes of the pulse rate are seen in the probe signal as well.

In FIG. 8b, the probe attenuation is observed to occur at the termination of apnea as well as during each of the three periods of apnea as in FIG. 8a. During one such apnea, a clear reduction in the arterial blood pressure was observed (area marked in black).

It can clearly be seen that when the attenuation of the probe signal occurs during the brief arousal at the end of the apnea (grey areas), an increase in the pulse rate, and a large increase in blood pressure also occur. The attenuation of the probe signal at such times reflects increased vascular resistance, which is associated with the increased blood pressure.

It is possible to consider the relationship of blood pressure, vascular resistance and cardiac output as being respectively analogous to voltage, resistance and current in Ohm's equation, such that cardiac output is proportional to the ratio between blood pressure and vascular resistance. Thus the increased blood pressure and increased vascular resistance as depicted in the attenuation of the probe signal, could occur in the absence of a change in cardiac output.

In contrast to this situation, a decrease in the probe signal without increased blood pressure could indicate a reduction in cardiac output. A reduction in the probe signal associated with a reduction in blood pressure (as seen in FIG. 8b), would be reflective of an even more substantial decrease in cardiac output.

It is unlikely that the changes in probe amplitude would be related to thermoregulatory affects, or other local regulatory effects, since their duration and repetitive nature are matched to the apnea cycles. It is possible to use the time interval between the appearance of ECG features, such as the QRS complex or the R wave, and features of the pulse-wave such as the peak or start of the upstroke, as an index of pulse transit time (PTT) which is known to be a surrogate of blood pressure. By comparing the PTT during episodes of probe signal attenuation to the intervening periods, it will be possible to differentiate between attenuation episodes associated with increased blood pressure and those not associated with increased blood pressure.

Detrended Fluctuation Analysis (DFA) is a known method for characterizing beat-to-beat variability for ECG heart rate pulses (Peng C-K, Hausdorff J M, Goldberger A L. Fractal mechanisms in neural control: Human heartbeat and gait dynamics in health and disease. In: Walleczek J. ed. Nonlinear Dynamics, Self-Organization, and Biomedicine. Cambridge: Cambridge University Press, 1999). The DFA method is described elsewhere (C.-K. Peng, S. V. Buldyrev, S. Havlin, M. Simons, H. E. Stanley, and A. L. Goldberger, Phys. Rev. E 49, 1685 (1994). The alpha value provided by this method represents an index related to variability.

It has been shown that by applying the DFA method to the signal outputted by the finger-probe described above, both the variability in the beat-to-beat pulse wave amplitude, and the pulse period, can be used for the detection of CHF (using the scaling alpha exponent alpha, which is the result of the DFA method), and that the diagnostic performance can be improved when using both DFA results applied to both amplitude and period of the time series.

FIG. 9 is a scatter-graph showing alpha values of interbeat period (pulse rate PR) plotted against alpha values of amplitude for CHF patients (stars) and for normal subjects (circles). It can be seen that the separation of the CHF and normal populations is enhanced when both values are considered.

64 subjects (30 normals, 34 CHFs) participated in the study. The area under the curve values for receiver operating characteristics defining the sensitivity and specificity at a range working points of the method for detection of CHF patients are listed in Table 1 below. Also given are corresponding p values.

TABLE 1

| Amp only | PR only | Both Amp & PR |
|---|---|---|
| 0.93 | 0.89 | 0.94 |
| P < 0.001 | p < 0.001 | PPR = 0.155; pAmp = 0.003 |

DFA has also previously been used for REM detection in ECG recording (Bunde A., Havlin S., Kantelhardt J. W., Penzel T., Peter J.-H. Peter, and Voigt K. Correlated and uncorrelated regions in heart-rate fluctuations during sleep, Physical Rev Lett Oct. 23, 2000;85(17) 3736-9).

It has been shown that by applying the DFA method to the signal outputted by the finger-probe, either the variability in the beat-to-beat pulse wave amplitude, or the pulse period, can be used for the detection of Rapid Eye Movement (REM) using the scaling exponent (alpha), which is the result of the DFA method. It has also been shown that diagnostic performance is improved when using the combined results of both DFA results from the probe output amplitude (alpha Amp) and period (alpha PR) time series.

25 subjects participated in the study. For each subject only the last REM and last NREM section (with at least 15 minutes) were analyzed.

The ROC area and the p-value for each test are listed in Table 2 below:

TABLE 2

| Amp only | PR only | Both Amp & PR |
|---|---|---|
| 0.89 | 0.90 | 0.94 |
| P = 0.001 | p < 0.001 | PPR = .004; pAmp = .008 |

Figure 10:
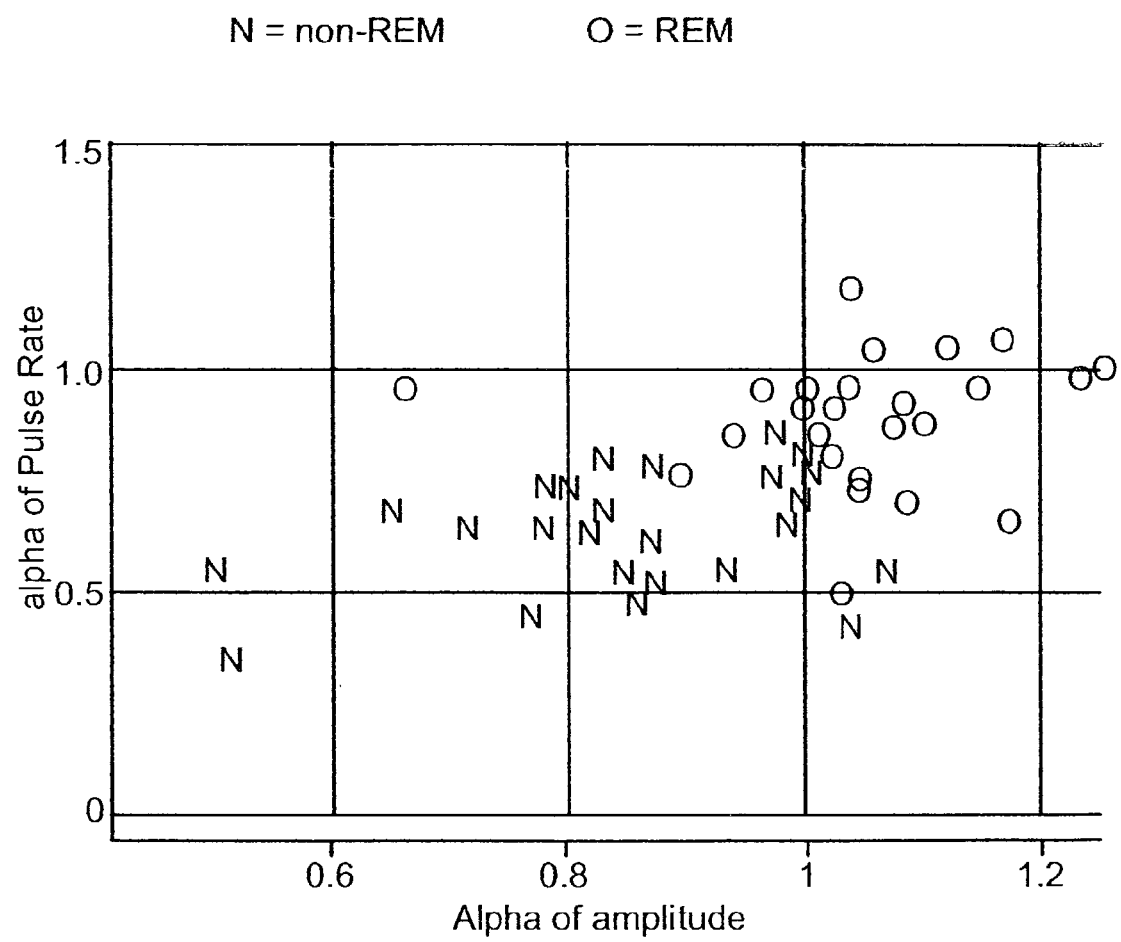
FIG. 10 is a scattergraph showing how the finger-probe output can be used in the known DFA method for the detection of rapid eye movement (REM) stage sleeping.

FIG. 10 is a scattergraph showing alphaPR plotted against alphaAmp for the N(non-REM) and O(REM) groups: It is clear that the combined use of both pulse rate alpha value and amplitude alpha values results in a better separation between the REM and non-REM sleep stages than was provided by either value alone.

Figure 11:
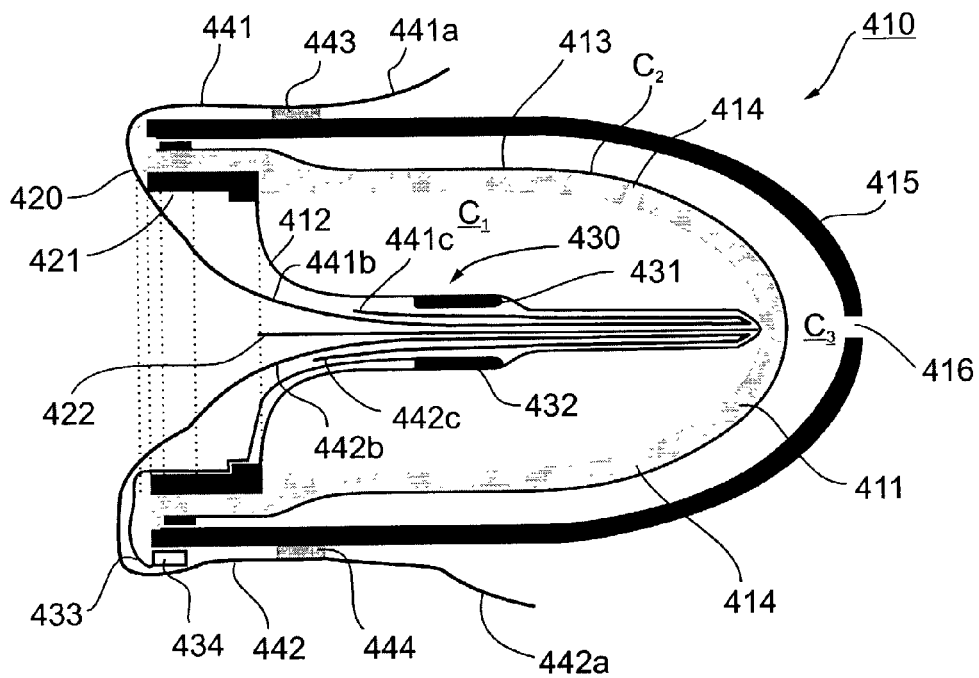
FIG. 11 illustrates a further type of finger probe, namely one using a self-contained fluid system, that may be used as the finger probe.
Figure 12:
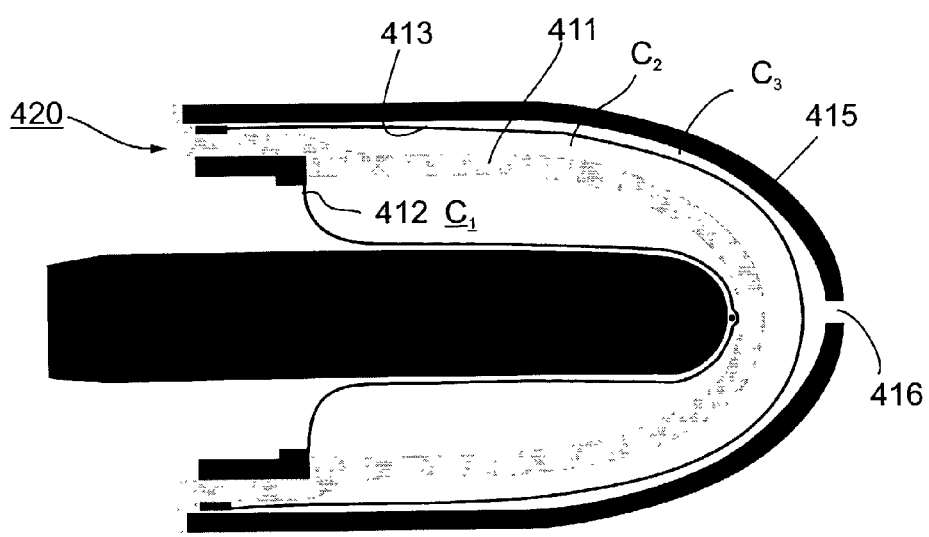
FIG. 12 illustrates the finger probe of FIG. 11 after removal of the liners provided in such a probe to facilitate the application of the probe to the subject's finger.

The Finger Probe Construction of FIGS. 11 and 12

FIGS. 11 and 12 illustrate a finger probe, generally designated 402, of a construction described in International Patent Application PCT/IL02/00249, filed Mar. 26, 2002, or in the earlier International Patent Application PCT/IL99/00292, published Dec. 16, 1999 as WO 99/63884. In the interest of brevity, FIGS. 11 and 12 of the present application show only the probe construction illustrated in FIGS. 1 and 2c, respectively, of International Application PCT/IL02/00249, but in the interest of completeness, the entire contents of the two above-identified International Applications are incorporated herein by reference. Such a probe includes a self-contained fluid system for applying the near diastolic pressure over the surface of the finger (or toe) to reduce the transmural pressure and also to provide a contiguous buffer region proximal to the detector site. FIG. 11 illustrates the probe including removable liners for facilitating the application of the probe to the patient's finger (or toe), as will be described more particularly below; whereas FIG. 12 illustrates the probe after it has been applied to the patient's finger (or toe) and the liners removed.

Briefly, probe 402 includes a housing containing an inner casing 411 of thimble shape to define a compartment closed at one end and open at the opposite end for receiving a subject's finger. Probe 402 further includes a first, inner membrane 412 defining, with the inner surface of casing 411, an inner chamber $C_1$ for receiving a fluid to apply a static pressure to the subject's finger when received within the compartment, and a second membrane 413 defining a second chamber $C_2$ communicating with the first chamber $C_1$ via openings 414 through casing 411.

As distinguished from the probe constructions illustrated in FIGS. 1 and 2, probe 402 in FIGS. 11 and 12 further includes an outer casing 415 defining a third chamber $C_3$ with the second membrane 413. This third chamber $C_3$ is vented to the atmosphere via an opening 416 formed in the outer casing 415. The provision of the outer casing 415, together with its vent opening 416, provides a number of important advantages as will be described more particularly below.

Probe 402 further includes a restraining member, generally designated 420, which is located within the compartment defined by casing 411 and membrane 412 for receiving the subject's finger. As described in the above-identified U.S. Patents and International Patent Applications, restraining member 420 restrains the inner membrane 412 from expelling the subject's finger from the compartment when chamber $C_1$ is pressurized. Restraining member 420 may be of any of the constructions described in the above-cited patents and applications, to include an annular ring 421 at the open end of the probe 402 and a bar 422 extending to the closed end of the compartment defined by the inner membrane 412 and inner casing 411.

Probe 402 further includes an optical sensor 430 for sensing changes in the optical characteristics of the finger inserted within the compartment of the probe. In this case, the optical sensor 430 senses the density of the light passing through the skin of the subject's finger inserted within the compartment, and therefore includes a light source 431 and a light detector 432 staggered up to 180° with respect to each other. In FIG. 11 they are shown as located on the opposite sides of the compartment such that the detector 432 is displaced 180° with respect to the light source 431. The light source 431 and detector 432 are externally connected to a measuring system by electrical leads 433 and a connector 434.

Probe 402 illustrated in FIG. 11 is further provided with two removable liners 441, 442 lining the inner surface of the compartment receiving the subject's finger. Each liner is of a low-friction sheet material to facilitate the insertion of the subject's finger into the compartment. Such liners are particularly useful in probes having a self-contained fluid for producing the near diastolic pressure applied to the finger. They facilitate the insertion of the subject's finger by providing low-friction surfaces between the finger and the inner membrane 412 under the static pressure. The low-friction property of the liners, together with the manner in which each is disposed between the subject's finger and the inner membrane 412, also facilitates the slidable withdrawal of each liner from between the subject's finger and the inner membrane.

The two liners 441 and 442 line the two inner surfaces of the housing compartment to face the opposite sides of the subject's finger when inserted therein. Each liner 441, 442 includes an external portion, as shown at 441a and 442a, respectively, extending externally of the outer casing 415, and an inner portion including two (or more) folded sections 441b, 441c and 442b, 442c, respectively, received within the compartment between the inner membrane 412 and the subject's finger when inserted into the compartment.

As shown in FIG. 11, the externally-extending portions 441a, 442a of the liners are temporarily adherent to the outer surface of the outer casing 415. This may be done by the provision of spots of adhesive 443, 444, between the respective liner and the outer casing.

FIG. 12 illustrates the condition of the probe 402 after both liners 441, 442 have been withdrawn. Providing the internal portion of each liner with the folded sections 441b, 441c and 442b, 442c, as illustrated in FIG. 11, facilitates the slidable withdrawal of each liner.

Including the outer casing 415 in probe 402 illustrated in FIGS. 11 and 12 produces a number of advantages. Thus, the outer casing 315 provides a rigid surface for adhering the removable liner strips 441, 442, e.g., at the adhesion points 443, 444. In addition, since the outer casing 415 encloses the outer membrane 413, it provides protection for that membrane, both during the use of the probe, and also during its handling and storage before use and between uses.

Further particulars as to the structure and the manner of using such a probe are available from the above-cited International Patent Applications PCT/IL99/00292 and PCT/IL02/00209, the contents of which are incorporated herein by reference; and further particulars as to the manner of using the probe of FIGS. 11 and 12, as well as those of FIGS. 1 and 2, for obtaining information as to the sleep state condition of the patient are available from the above-cited U.S. Pat. No. 6,319,205 and International Application PCT/IL01/00199, the contents of which are also incorporated herein by reference.

Figure 13:
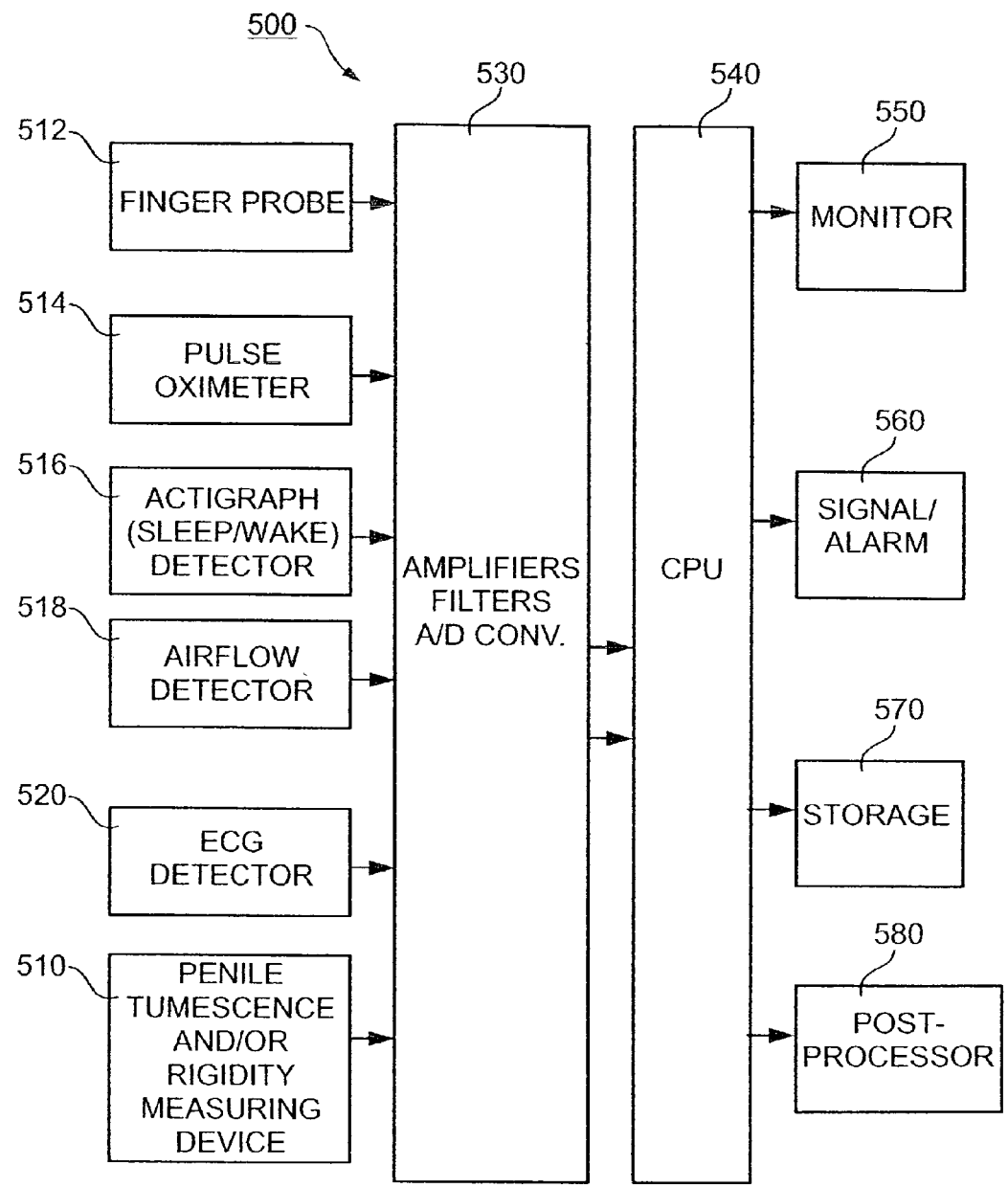
FIG. 13 is a block diagram illustrating one form of apparatus constructed in accordance with the present invention for producing information helpful in diagnosing the cause of a functional impotence condition in accordance with the method of the present invention.

Diagnosing a Functional Impotence Condition (FIG. 13)

FIG. 13 is a block diagram illustrating one form of apparatus constructed in accordance with the present invention for aiding in diagnosing the cause of a functional impotence condition in a male patient. Briefly, the apparatus illustrated in FIG. 13, and therein generally designated 500, includes a penile tumescence monitoring device, generally designated 510, for monitoring penile tumescence of the patient while sleeping to detect nocturnal penile erections. The illustrated apparatus further includes various sleep state monitoring devices, such as described above, for monitoring the sleep state condition of the patient while sleeping, particularly to detect frequency of awakenings, episodes of apnea, and/or REM sleep stages.

The sleep state monitoring devices illustrated in FIG. 13 a finger probe 512, which detects changes in the peripheral vascular system, particularly the peripheral arterial tone, of the patient while sleeping; a pulse oximeter 514 for detecting changes in the blood oxygen saturation level of the patient while sleeping; an actigraph 516, which serves as a sleep/wake detector for detecting the sleep/wake state of the patient; an airflow detector 518, for detecting changes in the oral or nasal airflow of the patient while sleeping; and an ECG electrode dipole 520 for detecting changes in the ECG signals of the patient. One or more of such monitoring devices 512-520 may be used in any desired combination. The outputs from monitoring devices 512-520 provide information regarding the sleep state condition of the patient, which information is helpful, with the information from the penile tumescence monitoring device 510, in diagnosing the cause of a functional impotence condition, i.e., whether the condition is more likely due to an organic cause or a psychogenic cause.

The penile tumescence monitoring device 510 may be any suitable device for measuring penile tumescence and/or rigidity, such as one of those described in the above-cited U.S. Pat. Nos. 6,162,188; 4,848,361 or 4,515,166. The penile rigidity monitoring device commercially available under the trade mark "RIGISCAN" has been found particularly useful for this purpose.

The finger probe 512 included in the apparatus of FIG. 13 is preferably one of the external finger probes illustrated in FIGS. 1, 2, 10 and 11 of the drawings in the present application, and more particularly described in the prior applications and patents identified in the description of the respective probe. Such probes provide, in a convenient and non-invasive manner, information as to the sleep state of the patient which information is very helpful in evaluating the information from the penile tumescence or rigidity monitoring devices 510 in diagnosing the cause of a functional impotence condition.

The pulse oximeter 514 monitors changes in the blood oxygen saturation level of the patient. This information is also useful, together with that supplied by the finger probe 512, in indicating the sleep state condition of the patient. Pulse oximeter 514, if used, may be incorporated in the finger probe 512, or may be used as a separate monitoring device. The actigraph 516 or other similar patient motion detector, serves as a sleep/wake detector for detecting the sleep/wake state of the patient. This device may be of a type commonly used in sleep medicine. The oral/nasal airflow detector 518 may be a thermistor or the like, as also known in polysomnographs, to measure the oral/nasal airflow of the sleeping patient. Such a detector, which is also optional in the illustrated apparatus, would provide further information supplementing that provided by the finger probe 512 for indicating the sleep state condition of the patient. Similarly, the ECG electrode dipole detector 520, as also commonly included in polysomnographs, detects the ECG signal of the patient, which information is also useful in determining the sleep state of the patient.

As further shown in FIG. 13, the outputs from the penile tumescence or rigidity monitoring device 510, together with the outputs from the other monitoring devices 512-520 for monitoring the sleep state condition of the patient, are converted to digital form by an A/D converter 530, and are fed to a processor 540. Processor processes this information and produces outputs to a monitor 550, a signal and/or alarm 560, a storage device 570, and a post-processor device 580.

Thus, penile tumescence or rigidity monitoring device 510 monitors penile tumescence and/or rigidity of the patient while sleeping to detect nocturnal penile erections, and for producing an output corresponding to the detected nocturnal penile erections. At the same time, finger probe 512 and the other sleep state monitoring devices 512-520 monitor the sleep state condition of the patient while sleeping to detect frequency of awakenings, episodes of apnea, and/or REM (rapid eye movement) sleep stages, and produce outputs corresponding to such detected sleep state condition. Processor 540 receives and processes the outputs of these monitoring devices and produces an output indicative of detected nocturnal penile erections time-correlated to the detected sleep state condition, to aid in determining whether the functional impotence condition in the patient is more likely due to an organic cause or to a psychogenic cause.

For example, a patient suffering from frequent awakenings or apnea episodes (cessation of breathing) during sleep, or a patient not able to sustain long periods of REM sleep, may not be experiencing sleep, particularly REM sleep, of sufficient duration for erection to occur. Thus, where nocturnal penile erections are not detected both during frequent awakenings, frequent apnea episodes, and/or short REM sleep, and also during infrequent awakenings, apnea episodes, and/or relatively long REM sleep, this would indicate an organic cause for the impotence condition. On the other hand, where nocturnal penile erections are not detected during frequent awakenings apnea episodes, and/or short REM sleep, but are detected during infrequent awakenings infrequent apnea episodes and/or long REM sleep, this would indicate a psychogenic cause for the impotence condition.

It is thus seen that such apparatus, providing sleep state information in addition to the penile tumescence and/or rigidity information, would be helpful in making the above diagnostic distinction between the possible causes of the impotence condition.

Diagnosing Hypoglycemia at Night

Hypoglycemia in type 1 diabetes mellitus is more common at night, but the reason therefor is not fully understood. One potential explanation is that sleep inhibits the counter-regulatory hormonal response to hypoglycemia, and therefore children do not have "alarming" signals when glucose levels decline during sleep.

The continuous subcutaneous glucose sensor has been shown to measure glucose levels accurately, at frequent intervals without causing sleep disruption. However, it is an invasive measurement associated with a traumatic insertion procedure and a degree of patient risk.

The above-described finger probe, based on measuring peripheral arterial tonometry (PAT) can be used to measure the time-course of digital pulsatile volume. Since the digital arteries are primarily innervated by the alpha adrenergic receptors, the PAT probe indirectly reflects the activation of the sympathetic nervous system. This method thus enables the detection of autonomic responses, including arousals during sleep, on a continuous basis without the need to draw blood or interfere with the natural sleep of the subject.

A study entitled "Paradoxical Effects of Hypoglycemia on Sleep Regulation in Children with Type 1 Diabetes Mellitus" by G. Pillar, G. Schuscheim, R. Weiss, A. Malhotra, A. Shlitner, N. Peled, N. Shehadeh was conducted to investigate the relationship between glucose concentrations as well as the rate of change of glucose concentration, sleep and adrenergic and arousal response to spontaneous nocturnal hypoglycemia. An abstract of this study appears in Journal of Sleep Research, 2002, 11 (Suppl. 1), 1-260, 359 O.

The following Table 3 summarizes the main findings of the study:

TABLE 3

Peripheral Arterial Tone (PAT) changes as a function of rate of blood glucose change.

|  | PAT detected awakenings | No PAT detected awakenings |
| --- | --- | --- |
| Rapid Glucose change (>50 mg/dL/h) | 7 | 8 |
| Slow Glucose change (25–50 mg/dL/h) | 1 | 14 |

From the above, it can be seen that in only 1 of 15 patients without rapid blood glucose changes had PAT detected arousals, while in 7 out of 15 patients with rapid blood glucose changes there were PAT detected awakenings. Thus, the occurrence of awakenings in a child with type 1 diabetes carries a high positive predictive value of 87.5% since seven out of eight cases of awakening occurred in patients with rapid blood glucose changes.

Monitoring the sleep state condition of a subject, particularly the peripheral arterial tone (PAT) during sleep as described above, can also be used as an aid in diagnosing or treating other medical conditions or disorders. Described below are several such diagnostic applications and their diagnostic relevance particularly, but not exclusively when the subject is a child.

Obstructive Sleep Apnea (OSA) in Children

Growth and development of children is dependent on sufficient sleep. Poor growth rate associated with adequate caloric intake (failure to thrive) is a frequent consequence of OSA in children. Children with OSA demonstrate significant decrease in energy expenditure during sleep following treatment for OSA. They increase weight and height following treatment (without a significant change in caloric intake). Development of children requires alertness while awake, and neuro-behavioral consequences of OSA in children are well established.

In the pediatric population, OSA is estimated to occur in 1-3% of children, but even higher prevalence was reported, depending on the diagnostic criteria used. Snoring is estimated to occur in 10% of all children and needs to be evaluated for potential OSA. Normal values in children are considered to be a Respiratory Disorder Index (RDI) of less than 1 event per hour, and oxygen saturation which does not fall to less than 92%. Since the RDI's in children can be low despite a potentially severe disorder, alternative clinically based severity criteria were suggested. According to these criteria, grade 0 indicates normal children, grades 1-2 indicate simple snoring and increased upper airway resistance, respectively, grade 3 reflects apneas/hypopneas without oxygen desaturations, grade 4 with oxygen desaturations, and grade 5 with complications (e.g. cor pulmonale, cardiomegaly, heart failure). In children, the peak occurrence of OSA is between the ages 2-5.

Symptoms in children are similar to those seen in adults, with the exception of restlessness that is a more common symptom in children, while sleepiness is somewhat less of a problem compared to adults. In children with OSA it is common that despite sleepiness they paradoxically demonstrate symptoms of attention deficit hyperactive disorder (ADHD). In fact, in a survey of 27 children with ADHD, 25% had OSA, and could have their ADHD eliminated by treating their sleep disordered breathing.

Clinical consequences of OSA in children include poor school achievements, failure to thrive, secondary enuresis, pulmonary and systemic hypertension, cor pulmonale, or congestive heart failure. Since childhood OSAS is usually associated with adenotonsillar hypertrophy, the majority of cases are amenable to surgical treatment. Adenotonsillectomy is the most common therapy for OSA in children. However, there is a substantial subgroup of children with OSA without hypertrophy of tonsils or adenoids. Furthermore, in some children OSA persist after adenotonsillectomy. Also, even children in whom OSA resolved after adenotonsillectomy may demonstrate recurrence during adolescence.

Thus, children with potential OSA need to be diagnosed and followed up. PSG is even more cumbersome in children than it is in adults and is frequently not performed. Many surgeons prefer to perform adenotonsilectomy but skip the PSG. For this reason, many surgeries are performed unjustifiably (not withstanding medical justifications other than OSA). It should be mentioned that the natural history of adenoids and tonsils is to shrink over time, so the condition resolves spontaneously over time in most untreated children.

By standard measures it seems that children arouse less than adults following apneas. It is possible that children do not demonstrate EEG arousals, but do demonstrate autonomic arousals following respiratory events, and thus the PAT may be more sensitive in diagnosing them.

Thus, children with potential OSA (about 10%) are a group in which the above-described technique for monitoring sleep state conditions can play a very important role.

Attention Deficit Hyperactive Disorder (ADHD) and Learning Disability

Attention deficit hyperactive disorder (ADHD) is a common psychobiological disorder of children, which can persist into adolescence and adulthood. ADHD classically consists of four characteristics: attention deficit, hyperactivity, distractibility and impulsivity. It usually affects approximately 4% of children, and usually 50% are diagnosed prior to the age of 5. Traditionally, ADHD was considered as a problem of over-alertness, nervousness, with the children affected being fidgety and over-stimulated. However, for a long time it has been well known that stimulating medications paradoxically result in improvement in the majority of the children.

Parents perceive children with ADHD to have greater sleep difficulty than normally developing children. In some recent studies it has been shown that children with ADHD have reduced sleep quality compared with control children. In-lab whole night polysomnographic evaluation of sleep in children with ADHD revealed relatively high incidences of primary sleep disorders such as obstructive sleep apnea (OSA) or periodic limb movement (PLM) disorder of sleep. Likewise, it is well known that sleepy children due to sleep disturbances may demonstrate hyperactivity and attention deficit rather than excessive daytime somnolence.

Thus, it is possible that despite the overactivity and irritability children with ADHD demonstrate, in fact these children are sleepy. This can be a result of sleep disruption and non-restorative sleep, and may explain the effectiveness of stimulating medications. For this reason, it is now believed (although progressing slowly) that every child with abnormal behavior or learning disability should undergo a sleep evaluation.

Silent Nocturnal Asthma

The prevalence of asthma in children is 5% or more. About 10-20% of affected children have increased nocturnal asthmatic activity (bronchoconstriction), which is not dramatic enough to take them to their doctor but may interfere with their sleep and result in growth retardation and learning disabilities. Thus, in asthmatic children the method of the present invention may be useful in recognizing nocturnal asthmatic activity and, consequently, for improving medical therapy. Similar considerations apply for adults with the exception of the detrimental developmental aspects related to children.

Sleep Terrors

Sleep terrors are characterized by sudden arousals from sleep with piercing screams and intense fear manifested by heightened sympathetic activation (tachycardia, diaphoresis, flushing of the skin, mydriasis, and hyperpnea). The typical age for this condition is 4-12 years, peaking at age 5-7, with an approximate prevalence of 3-4% in this age group. This declines to less than 1% in adults. During such an event the child is unresponsive and confused as in other disorders of arousal. Once fully alert, the patient is generally amnestic to the sleep event, and does not have a recollection of a dream. This is one of the classical differences between sleep terrors and nightmares. The distinction between them is important for prognostic and further evaluation purposes. That is, in cases of recurrent nightmares a psychological evaluation may be indicated to rule out stress, trauma (abuse) or personality disorder, while in sleep terrors sometimes EEG is required to rule out temporal or frontal lobe epilepsy. Usually the distinction between sleep terrors and nightmares can be made by history alone, but in some cases a full polysomnographic study is required. In these cases the PAT may be useful since it can distinguish between the REM and non-REM sleep in addition to detecting the intense sympathetic storm in sleep terrors.

As indicated earlier, the finger probes described above which measure changes in the peripheral arterial bed volume, have been found to produce the best results in detecting the various sleep state conditions in accordance with the present invention. However, it will be appreciated that the detection of the various sleep state conditions described can also be effected by other means or by the use of other non-invasive probes which measure the peripheral vascular bed volume, and that many other variations, modifications and applications of the invention may be made.

What is claimed is:

1. A method of monitoring an individual for the occurrence of a particular sleep state condition of the individual, comprising:

applying an external probe to an external surface at a peripheral body location on the individual's body for monitoring the peripheral vascular bed volume of the individual at said peripheral body location while applying a predetermined pressure field to the distal end of said peripheral body location, including its distal-most extremity, effective to prevent the occurrence of venous pooling within said peripheral body location, and thereby to produce an output from the probe corresponding to changes in the peripheral arterial bed volume at said peripheral body location;

while the individual is in a sleep state, utilizing said probe to detect: (a) changes in the peripheral vascular bed volume of the individual at said peripheral body location, (b) amplitude changes in the probe output or time changes in the time course of the response pattern of the probe output, and (c) changes in the individual's pulse rate or amplitude, and to produce outputs corresponding to such changes;

and determining the sleep state condition of the individual according to such changes detected by said external probe.

2. The method according to claim 1, wherein said pressure field is extended for a distance from said monitoring site towards the heart side of said peripheral body location such as to prevent the occurrence of venous pooling also thereat.

3. The method according to claim 2, wherein said external probe measures changes in the peripheral arterial tone at said peripheral body location.

4. The method according to claim 1, wherein said peripheral body location of the individual is a finger, toe or ear lobe of the individual.

5. The method according to claim 1, wherein said external probe is a volume measuring device.

6. The method according to claim 1, wherein said external probe is an optical density measuring device.

7. The method according to claim 1, wherein said particular condition is an arousal during the sleep state, and is indicated at least by a predetermined attenuation in the probe output.

8. The method according to claim 7, wherein the time intervals between attenuations in the probe output are also used to determine the sleep state condition of the individual.

9. The method according to claim 1, wherein said particular condition is an apnea event and is indicated at least by a predetermined attenuation in the probe output.

10. The method according to claim 1, wherein said particular condition is a hypopnea event and is indicated at least by a predetermined attenuation in the probe output.

11. The method according to claim 1, wherein said particular condition is an upper airway resistance syndrome (UARS) event and is indicated at least by a predetermined attenuation in the probe output.

12. The method according to claim 1, wherein said particular condition is a Cheyne-Stokes breathing pattern and is indicated at least by predetermined attenuations in the probe output.

13. The method according to claim 1, wherein said particular condition is a REM (rapid eye movements) sleep stage condition and is indicated at least by predetermined attenuations in the probe output.

14. The method according to claim 1, wherein the time intervals between attenuations in the probe output are used to distinguish between arousals related to periodic leg movement syndrome (PLMS) and arousals related to disordered breathing events during sleep.

15. The method according to claim 1, wherein the blood oxygen saturation level of the individual is also monitored to produce an output which is used with the output of said external probe to determine the sleep state condition of the individual.

16. The method according to claim 1, wherein, the oral-nasal airflow of the individual is also monitored to produce an output which is used with the output of said external probe to determine the sleep state condition of the individual.

17. The method according to claim 1, wherein, the ECG pulse of the individual is also monitored to produce an output which is used with the output of said external probe to determine the sleep state condition of the individual and particularly the Pulse Transition Time (PTT).

18. The method according to claim 1, wherein:
the individual is an adult male suffering from a functional impotence condition;
while the individual is in said sleep state condition, a penile tumescence or rigidity monitoring device is utilized to also detect nocturnal penile erections and to produce an output corresponding thereto;
and the outputs of said probe and said penile tumescence monitoring device are utilized in determining whether the impotence condition of the individual is more likely due to an organic cause or a psychogenic cause.

19. The method according to claim 1, wherein: the individual is a diabetic patient and the output of said probe is utilized in indicating the probable occurrence of abrupt changes in the glucose level of the patient.

20. The method according to claim 1, wherein the individual is a child, and the output of said probe is utilized in detecting a potential obstructive sleep apnea (OSA) condition in the child.

21. The method according to claim 1, wherein the individual is a child suffering from Attention Deficit Hyperactive Disorder (ADHD) condition, and the output of said probe is utilized in diagnosing the cause of said AHDH condition of the child.

22. The method according to claim 1, wherein the individual is a child, and the output of said probe is utilized in detecting a silent nocturnal asthma condition in the child.

23. The method according to claim 1, wherein the individual is a child, and the output of said probe is utilized in distinguishing between sleep terrors and nightmares.

24. The method according to claim 1, wherein said peripheral body location of the individual is a superficial skin region of the individual's body surface.

25. The method according to claim 1, wherein said predetermined change of the probe output or said predetermined change in the time course of the response pattern of the probe output is derived from a series of pulse waves for determining the sleep state condition of the individual.

26. The method according to claim 1, wherein said predetermined change of the probe output or said predetermined change in the time course of the response pattern of the probe output is derived from the variability of a series of pulse waves for determining the sleep state condition of the individual.

27. The method according to claim 1, wherein said particular condition is arousals or respiratory disorders in a CPAP treated patient.

28. The method according to claim 27, wherein said output of the external probe is also used to differentiate between respiratory and non-respiratory arousals.

29. Apparatus for monitoring an individual to detect the occurrence of a particular condition during the sleep state of the individual, comprising:
an external probe to be applied to an external surface at a peripheral body location on the individual's body for monitoring (a) changes in the peripheral vascular bed volume of the individual at said peripheral body location, (b) amplitude changes in the probe output or changes in the time course of the response pattern of the probe output, and (c) changes in the individual's pulse rate and amplitude, and for producing outputs corresponding thereto;
said external probe including a pressure applicator for applying a predetermined pressure field to the distal end of said peripheral body location including its distal-most extremity to prevent the occurrence of venous pooling and thereby to produce an output signal from the probe corresponding to changes in the peripheral arterial bed volume at said peripheral body location;
and a processor for processing said outputs from the probe and for producing a signal indicating said particular sleep state condition when a predetermined change in the outputs of said probe is detected.

30. The apparatus according to claim 29, wherein said probe extends said pressure field for a distance from the signaling device towards the heart side of said peripheral body location such as to prevent the occurrence of venous pooling also thereat.

31. The apparatus according to claim 29, wherein said external probe measures changes in the peripheral arterial tone at said peripheral body location.

32. The apparatus according to claim 29, wherein said peripheral body location of the individual is a finger, toe or ear lobe of the individual.

33. The apparatus according to claim 29, wherein said external probe is a volume measuring device capable of providing an index related to volume.

34. The apparatus according to claim 29, wherein said external probe is an optical density measuring device.

35. The apparatus according to claim 29, wherein the apparatus further includes a pulse oximeter for monitoring the blood oxygen saturation level of the individual to produce an output which is used by said processor with said external probe output to indicate the sleep state condition of the individual.

36. The apparatus according to claim 29, wherein the apparatus further includes an oral-nasal airflow sensor for monitoring the oral-nasal airflow of the individual to produce an output which is used by said processor with said external probe output to indicate the sleep state condition of the individual.

37. The apparatus according to claim 29, wherein said individual is an adult male suffering from a functional impotence condition, and said apparatus further comprises: a penile tumescence or rigidity monitoring device for detecting nocturnal penile erections and for producing an output corresponding thereto, said probe and monitoring device outputs being helpful in diagnosing the cause of said functional impotence condition.

38. The apparatus according to claim 29, wherein said individual is a diabetic patient, and said processor processes the output of said probe to indicate the probable occurrence of abrupt changes in the blood glucose level of the patient.

39. The apparatus of claim 29, further comprising means for activating or de-activating of the said pressure applicator for applying a predetermined pressure field to the distal end of the peripheral body location of the external probe, wherein said activating or de-activating means are situated at the site of the said external probe itself.

\* \* \* \* \*